(12) United States Patent
Dewey et al.

(10) Patent No.: US 10,849,789 B2
(45) Date of Patent: Dec. 1, 2020

(54) METHODS AND SYSTEMS FOR OPHTHALMIC MEASUREMENTS AND LASER SURGERY AND METHODS AND SYSTEMS FOR SURGICAL PLANNING BASED THEREON

(71) Applicant: AMO Development, LLC, Santa Ana, CA (US)

(72) Inventors: David A. Dewey, Sunnyvale, CA (US); Javier G. Gonzalez, Palo Alto, CA (US); Georg Schuele, Portolla Valley, CA (US); David D. Scott, Oakland, CA (US)

(73) Assignee: AMO Development, LLC, Santa Ana, CA (US)

(*) Notice: Subject to any disclaimer, the term of this patent is extended or adjusted under 35 U.S.C. 154(b) by 501 days.

(21) Appl. No.: 15/269,781

(22) Filed: Sep. 19, 2016

(65) Prior Publication Data

US 2017/0189233 A1     Jul. 6, 2017

Related U.S. Application Data

(63) Continuation-in-part of application No. 14/327,839, filed on Jul. 10, 2014, now Pat. No. 10,646,116.
(Continued)

(51) Int. Cl.
*A61F 9/008* (2006.01)
*A61B 3/00* (2006.01)
(Continued)

(52) U.S. Cl.
CPC ........ *A61F 9/00827* (2013.01); *A61B 3/0025* (2013.01); *A61B 3/10* (2013.01);
(Continued)

(58) Field of Classification Search
CPC .. A61F 9/008; A61F 9/00804; A61F 9/00812; A61F 9/00825; A61F 9/00834;
(Continued)

(56) References Cited

U.S. PATENT DOCUMENTS 5,459,570 A    10/1995  Swanson et al.
5,720,894 A    2/1998   Neev et al.
(Continued)

FOREIGN PATENT DOCUMENTS

DE    202012002375 U1    4/2012
GB        2409033 A       6/2005
(Continued)

OTHER PUBLICATIONS

International Search Report and Written Opinion for Application No. PCT/US2016/052543, dated Jun. 13, 2017, 13 pages.
(Continued)

*Primary Examiner* — Ahmed M Farah
(74) *Attorney, Agent, or Firm* — Johnson & Johnson Surgical Vision, Inc.

(57) ABSTRACT

An ophthalmic measurement and laser surgery system includes: a laser source; a corneal topography subsystem; an axis determining subsystem; a ranging subsystem comprising an Optical Coherence Tomographer (OCT); and a refractive index determining subsystem. All of the subsystems are under the operative control of a controller. The controller is configure to: operate the corneal topography subsystem to obtain corneal surface information; operate the axis determining subsystem to identify one or more ophthalmic axes of the eye; operate the OCT to sequentially scan the eye in a plurality of OCT scan patterns, the plurality of scan patterns configured to determine an axial length of the eye; operate the refractive index determining subsystem so to determine an index of refraction of one or more ophthalmic
(Continued)

tissues, wherein at least one of the corneal surface information, ophthalmic axis information, and axial length is modified based on the determined index of refraction.

21 Claims, 24 Drawing Sheets

Related U.S. Application Data

(60) Provisional application No. 61/858,445, filed on Jul. 25, 2013.

(51) Int. Cl.
| | | |
|---|---|---|
| *A61B 3/107* | (2006.01) | |
| *A61B 3/103* | (2006.01) | |
| *G01M 11/02* | (2006.01) | |
| *A61B 3/10* | (2006.01) | |
| *G01N 21/45* | (2006.01) | |

(52) U.S. Cl.
CPC ............. *A61B 3/103* (2013.01); *A61B 3/107* (2013.01); *A61F 9/00825* (2013.01); *G01M 11/0228* (2013.01); *A61B 3/102* (2013.01); *A61B 3/1005* (2013.01); *A61F 9/00834* (2013.01); *A61F 2009/0087* (2013.01); *A61F 2009/00851* (2013.01); *A61F 2009/00872* (2013.01); *A61F 2009/00882* (2013.01); *A61F 2009/00887* (2013.01); *G01N 21/45* (2013.01)

(58) Field of Classification Search
CPC .............. A61F 9/00844; A61F 9/00851; A61F 2009/00861; A61F 2009/0087; A61F 2009/00872; A61F 2009/00874; A61F 2009/00878; A61F 2009/00882; A61F 2009/00887; A61F 2009/00889; A61F 2009/00897; A61B 3/10; A61B 3/1005; A61B 3/102; A61B 3/103; A61B 3/107; A61B 3/117; A61B 3/1173; G01N 21/41; G01N 2021/41; G01N 21/4133; G01N 21/45
USPC ....... 606/4–6, 10–12; 351/205–212; 128/898
See application file for complete search history.

(56) References Cited

U.S. PATENT DOCUMENTS

| | | | |
|---|---|---|---|
| 5,748,352 A | 5/1998 | Hattori | |
| 5,748,898 A | 5/1998 | Ueda | |
| 5,957,915 A | 9/1999 | Trost | |
| 5,984,916 A | 11/1999 | Lai | |
| 6,019,472 A | 2/2000 | Koester et al. | |
| 6,053,613 A | 4/2000 | Wei et al. | |
| 6,111,645 A | 8/2000 | Tearney et al. | |
| 6,454,761 B1 | 9/2002 | Freedman | |
| 6,508,960 B1 | 1/2003 | Ohmer et al. | |
| 7,217,375 B2 | 5/2007 | Lai | |
| 7,655,002 B2 | 2/2010 | Myers et al. | |
| 7,717,907 B2 | 5/2010 | Ruiz et al. | |
| 8,218,152 B1 | 7/2012 | Marks et al. | |
| 8,262,646 B2 | 9/2012 | Frey et al. | |
| 8,350,183 B2 | 1/2013 | Vogel et al. | |
| 8,377,047 B2 | 2/2013 | Dai | |
| 8,382,745 B2 | 2/2013 | Naranjo-Tackman et al. | |
| 8,414,564 B2 | 4/2013 | Goldshleger et al. | |
| 8,500,724 B2 | 8/2013 | Blumenkranz et al. | |
| 9,721,351 B2 * | 8/2017 | Gonzalez | A61B 3/145 |
| 9,996,938 B2 * | 6/2018 | Gonzalez | A61B 3/145 |
| 10,085,886 B2 * | 10/2018 | Schuele | A61F 9/008 |
| 10,190,977 B2 | 1/2019 | Marcus et al. | |
| 10,369,053 B2 * | 8/2019 | Srinivasan | A61F 9/00827 |
| 10,485,704 B2 | 11/2019 | Bareket et al. | |
| 10,506,923 B2 * | 12/2019 | Neal | A61B 3/112 |
| 2005/0203422 A1 | 9/2005 | Wei | |
| 2006/0206102 A1 | 9/2006 | Shimmick | |
| 2008/0033408 A1 | 2/2008 | Bueler et al. | |
| 2008/0039825 A1 | 2/2008 | Lai | |
| 2008/0281303 A1 | 11/2008 | Culbertson et al. | |
| 2009/0242021 A1 | 10/2009 | Petkie et al. | |
| 2010/0171865 A1 | 7/2010 | Toda | |
| 2011/0319873 A1 | 12/2011 | Raksi et al. | |
| 2011/0319875 A1 | 12/2011 | Loesel et al. | |
| 2012/0069298 A1 | 3/2012 | Ng | |
| 2012/0120408 A1 | 5/2012 | Yasuno et al. | |
| 2012/0268714 A1 | 10/2012 | Cameron et al. | |
| 2013/0165911 A1 | 6/2013 | Raksi et al. | |
| 2014/0343541 A1 | 11/2014 | Scott et al. | |
| 2015/0018674 A1 * | 1/2015 | Scott | A61F 9/00827 600/427 |
| 2015/0141972 A1 | 5/2015 | Woodley et al. | |
| 2020/0085622 A1 * | 3/2020 | Scott | A61B 5/0073 |

FOREIGN PATENT DOCUMENTS

| | | |
|---|---|---|
| JP | 2003052632 A | 2/2003 |
| JP | 2011502585 A | 1/2011 |
| JP | 2012521237 A | 9/2012 |
| JP | 2013517844 A | 5/2013 |
| JP | 2013520236 A | 6/2013 |
| WO | 2015013044 A1 | 1/2015 |
| WO | 2016061454 A1 | 4/2016 |

OTHER PUBLICATIONS

International Search Report and Written Opinion for Application No. PCT/US2014/046113, dated Oct. 10, 2014, 3 pages.

* cited by examiner

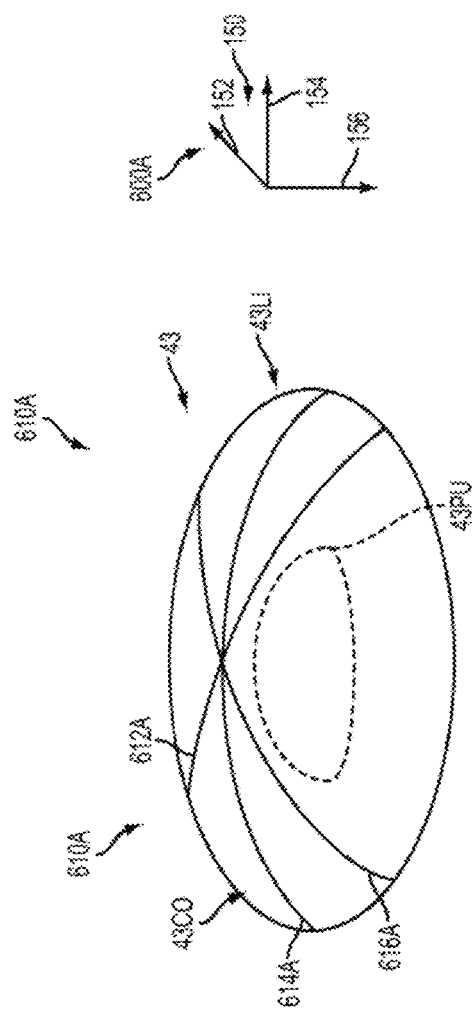
FIG. 6A1
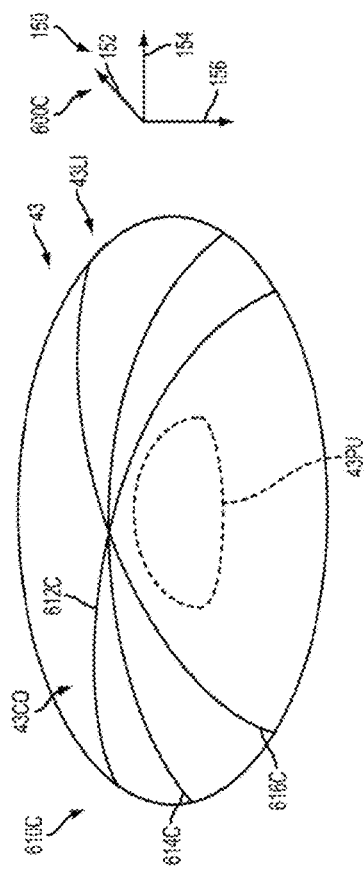
FIG. 6C1

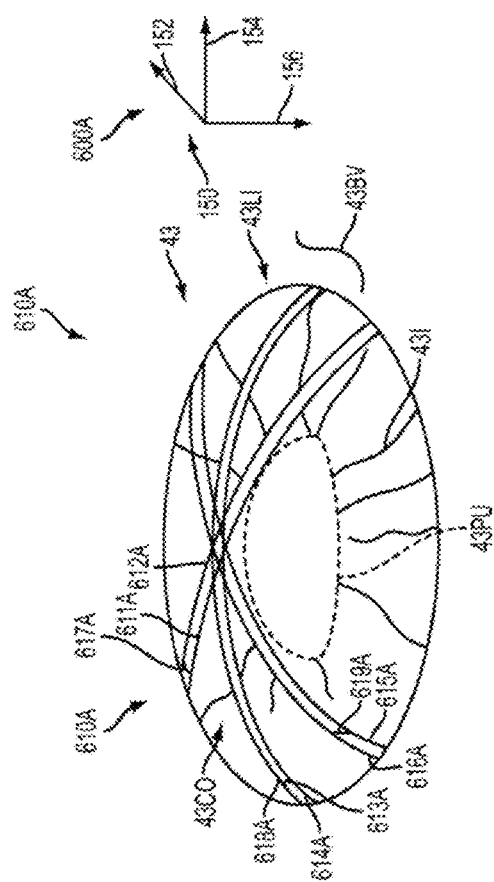
FIG. 6A2
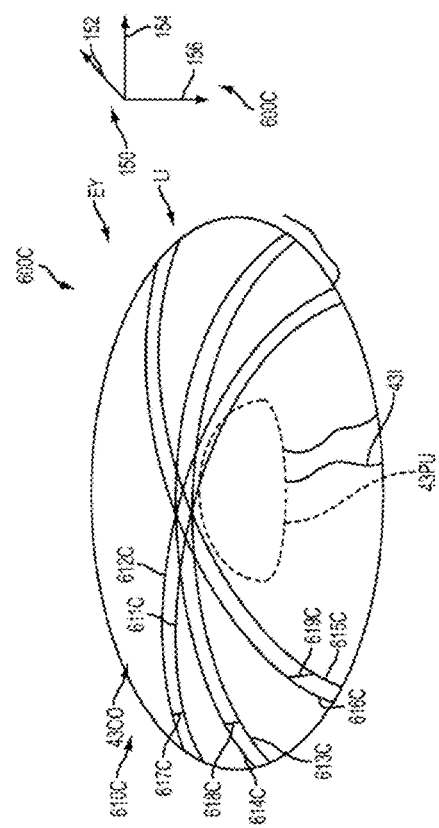
FIG. 6C2

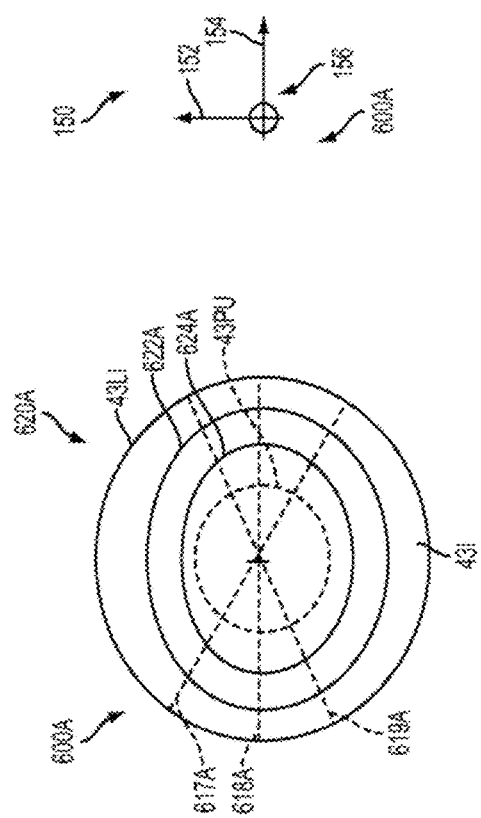
FIG. 6A3
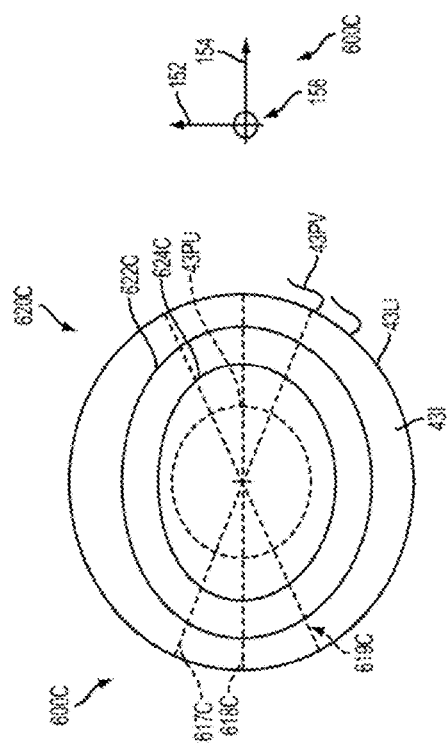
FIG. 6C3

METHODS AND SYSTEMS FOR OPHTHALMIC MEASUREMENTS AND LASER SURGERY AND METHODS AND SYSTEMS FOR SURGICAL PLANNING BASED THEREON

CROSS-REFERENCE

This application is a continuation-in-part of U.S. patent application Ser. No. 14/327,839, filed Jul. 10, 2014, which claims the benefit of priority to U.S. Provisional Patent Application No. 61/858,445, filed on Jul. 25, 2013, which is related to the following patent applications: U.S. patent application Ser. No. 12/048,182, filed Mar. 3, 2008, entitled "METHOD AND APPARATUS FOR CREATING INCISIONS TO IMPROVE INTRAOCULAR LENS PLACEMENT," U.S. patent application Ser. No. 12/048,186, filed Mar. 13, 2008, entitled "METHOD AND APPARATUS FOR CREATING OCULAR SURGICAL AND RELAXING INCISIONS," and U.S. Patent Application No. 61/722,064, filed Nov. 2, 2012, entitled "LASER EYE SURGERY SYSTEM CALIBRATION," the entirety of all of which are hereby incorporated by reference.

BACKGROUND

The eyes of many patients have structural features that result in less than ideal optical characteristics. At least some patients have refractive errors of the eye such as myopia, hyperopia and astigmatism. These refractive conditions can be corrected with spectacles or contact lenses. Alternatively, the cornea of the patient's eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures. The reason eye surgeons prefer a surgical laser beam over manual tools like microkeratomes and forceps is that the laser beam can be focused precisely on extremely small amounts of ocular tissue, thereby enhancing accuracy and reliability of the procedure. These in turn enable better wound healing and recovery following surgery. Surgical approaches for reshaping the cornea include laser assisted in situ keratomileusis (hereinafter "LASIK"), and photorefractive keratectomy (hereinafter "PRK").

Besides refractive errors, some patients may have an irregularity of the cornea of eye such as irregular astigmatism or corneal scarring for example. In at least some instances, the irregularity of the eye may not be easily corrected with prior methods and apparatus. Prior approaches to treating the diseased cornea have included keratoplasty, such as penetrating keratoplasty (hereinafter "PK"), for example. The prior keratoplasty procedures can result in less than ideal patient outcomes in at least some instances. For example, patients may have less than ideal visual acuity after keratoplasty procedures. In at least some instances, such less than ideal visual acuity may be caused than less than ideal positioning and location of tissue cuts.

Prior short pulse laser systems have been used to cut tissue, and have been used to treat many patients. However, the prior short pulse systems may provide less than ideal results in at least some instances. For example, the alignment of the eye with the laser surgery system can be less than ideal in at least some instances, such as when refractive treatment of the cornea of the eye is combined with a treatment of the lens of the eye such as removal of the cortex and nucleus from the eye. In another example, the laser eye surgery system may not properly take into account the different indices of refraction of the eye anatomy in at least some instances, which may affect the positioning of tissue cuts in at least some instances.

In order to more accurately treat the eye, prior methods and apparatus have combined optical measurement systems such as tomography systems. However, the accuracy of such prior measurement devices can be less than ideal in at least some instances. For example, to determine the physical location of a structure, the prior devices may rely on an assumed index of refraction which can vary from the actual index of refraction of the particular eye of an individual being treated. Further, at least some prior devices may rely on an assumed average value of the index of refraction for tissues that have a varying index of refraction such as tissue of the lens. The amount of variation of the index of refraction within an individual may vary more, or less, than normative values for a population, potentially making assumed values less accurate in at least some instances. In at least some instances, the treatment beam may comprise different wavelengths than the measurement beam, potentially further compounding the errors in the measurements in at least some instances.

The decreased accuracy of the prior methods an apparatus may limit, in at least some respects, the treatment of the prior methods and apparatus. For example, variability of the index of refraction may result in variability of the depth at which tissue is incised, thereby potentially decreasing the accuracy of the prior surgical procedures and potentially limiting the use of lasers to incise tissue near sensitive.

In light of the above, it would be desirable to provide improved methods and apparatus that overcome at least some of the above limitations of the above prior systems and methods. Ideally, these improved systems and methods will provide in situ measurement of the index of refraction of optically transmissive materials, provide improved measurement of the location of structures within the optically transmissive materials, to provide improved treatment with more accurate focus of laser beams within the material and to provide better and more accurate surgical and treatment planning.

SUMMARY OF THE INVENTION

Hence, to obviate one or more problems due to limitations and disadvantages of the related art, this disclosure provides many embodiments where, an ophthalmic measurement and laser surgery system, comprises: a laser source configured to produce a pulsed laser beam; a corneal topography subsystem; an axis determining subsystem; a ranging subsystem comprising an Optical Coherence Tomographer (OCT); and a refractive index determining subsystem. Each of the laser source, the corneal topography subsystem, the axis determining subsystem, and the refractive index determining subsystem under the operative control of a controller, wherein the controller is configure to: operate the corneal topography subsystem to obtain corneal surface information; operate the axis determining subsystem to identify one or more ophthalmic axes of the eye; operate the OCT to sequentially scan the eye in a plurality of OCT scan patterns, the plurality of scan patterns configured to determine an axial length of the eye; operate the refractive index determining subsystem so to determine an index of refraction of one or more ophthalmic tissues. At least one of the corneal surface information, ophthalmic axis information, and axial length is modified based on the determined index of refraction.

In many embodiments, the present invention comprises methods for improved ophthalmic and biometric measurements comprising one or more steps carried out by the laser surgery system or controller of the laser surgical system. The methods of the present invention may include: obtaining corneal surface information; identifying one or more ophthalmic axes of the eye; scanning the eye in a plurality of OCT scan patterns, the plurality of scan patterns configured to determine an axial length of the eye; and determine an index of refraction of one or more ophthalmic tissues. At least one of the corneal surface information, ophthalmic axis information, and axial length is modified based on the determined index of refraction.

In many embodiments, the corneal surface information comprises one or more selected from the group consisting of anterior corneal surface information and posterior corneal surface information.

In many embodiments, the controller is further configured to perform a plurality of OCT scan patterns comprising a lenticular OCT scan segment scan pattern suitable to measure a plurality lens information selected from the group consisting of a lens thickness, an anterior lens surface, a posterior lens surface, and a lens equator. In many embodiments, at least one of the lens information, the corneal surface information, ophthalmic axis information, and axial length is modified based on the determined index of refraction, thereby obtaining modified structural information. The modified structural information has improved accuracy over prior art methods.

In many embodiments, the controller is configured to construct a model of the eye based on modified structural information and one or more of the lens information, the corneal surface information, and the ophthalmic axis. In many embodiments, the model is performed using ray tracing.

In many embodiments, the one or more ophthalmic axes are selected from the group consisting of an optical axis, a treatment axis a visual axis and a fiducial marker axis.

In many embodiments, the controller is configured to sequentially scan the eye in a plurality of OCT scan patterns, each scan pattern being at a different axial depth of a patient's eye. The plurality of imaging scan patterns may comprise an anterior segment OCT scan pattern suitable to measure corneal surface information of a plurality of an anterior corneal surface, a posterior corneal surface, a corneal pachymetry, a central corneal thickness, and anterior chamber depth of a patient's eye. The selected corneal information so measured may be modified based in part on a determined index of refraction. The plurality of imaging scan patterns may comprise a lenticular OCT scan segment scan pattern suitable to measure lens information of a plurality of a lens thickness, an anterior lens surface, a posterior lens surface, and a lens equator. The lens information so measured may be modified based on a determined index of refraction. The plurality of imaging scan patterns comprise an retinal OCT segment scan pattern suitable to measure at least one of an axial length and retinal layer thickness information. The selected ones of the axial length and the retinal layer may be modified based on a determined index of refraction.

In many embodiments, the ophthalmic tissue comprises an optically transmissive tissue structure of an eye of a subject. The optically transmissive tissue structure of the eye comprises one or more of a tear film, a cornea, an aqueous humor, a lens, an anterior lens capsule, a lens cortex, an anterior portion of the lens cortex, a posterior portion of the lens cortex, a lens nucleus, a posterior lens capsule, or a vitreous humor.

In many embodiments, the system comprises a processor; and a memory operable to store data acquired from each of the corneal topography subsystem, the axis determining subsystem, and the OCT, wherein the stored data includes a plurality of corneal and lens surface information, the axis information, and the axial length of the eye.

In many embodiments, the memory operable to store Intraocular Lens ("IOL") Data, the IOL data including a plurality of dioptic power, anterior and posterior radius, IOL thickness, refractive index and dispersion, asphericity, toricity, echelette features, haptic angulation and lens filter.

In many embodiments, the system is configured to select an optimized IOL characteristic or IOL model.

In some embodiments, for each of Intraocular Lens ("IOL") model having associated with it a plurality of predetermined parameters selected from the group consisting of dioptic power, refractive index and dispersion, anterior and posterior radius, IOL thickness, asphericity, toricity, echelette design, haptic angulation and lens filter, the controller is programmed to execute a program to:

(1) model the subject eye with the intraocular lens based in part on the stored data;

(2) simulate the subject eye based on the plurality of IOL predetermined parameters and the predicted IOL position;

(3) perform a ray tracing and, optionally an IOL spherical equivalent (SE) and cylinder (C) power calculation, as well as determine the optimum IOL orientation based on said eye model; and (4) identify one IOL power for one or more IOL models from the plurality of IOLs corresponding to the optimized IOL(s) based on predetermined criteria.

In many embodiments, the modeling of the subject eye is performed with the IOL position with the equator of the IOL lens positioned at the same location of the equator of the lens of the subject eye. The modeling of the subject eye may also be performed with the haptics of the IOL located at the same location as the equator of the lens of the subject eye In some embodiments for each of Intraocular Lens ("IOL") model having associated with it a plurality of predetermined parameters selected from the group consisting of dioptic power, refractive index and dispersion, anterior and posterior radius, IOL thickness, asphericity, toricity, echelette design, haptic angulation and lens filter, the controller is programmed to execute a program to:

(1) modeling the subject eye with the intraocular lens based on the stored data;

(2) simulating the subject eye based on the plurality of IOL predetermined parameters and the predicted IOL position;

(3) perform a ray tracing and, optionally, an IOL spherical equivalent (SE) and cylinder (C) power calculation, as well as determine the optimum IOL orientation based on said eye model; and (4) identify one IOL model from the plurality of IOLs corresponding to the optimized IOL based on predetermined criteria.

In many embodiments, the system further comprises a scanning system, wherein the controller is configured to operate the scanning system to deflect the laser beam to in one or more treatment patterns, the treatment pattern configured so to incise in one or more ocular tissues in the eye of the patient.

In some embodiments, the one or more treatment patterns is a capsulotomy treatment pattern configured to incise a capsulotomy in the lens capsule.

In some embodiments, the one or more treatment patterns is a lens fragmentation treatment pattern configured to fragment the lens.

In some embodiments, the one or more treatment patterns is a relaxing incision treatment pattern.

In some embodiments, the one or more treatment patterns is a cataract incision treatment pattern.

In some embodiments, the one or more treatment patterns is a sideport incision treatment pattern.

This summary and the following detailed description are merely exemplary, illustrative, and explanatory, and are not intended to limit, but to provide further explanation of the embodiments as claimed. Additional features and advantages of the embodiments will be set forth in the descriptions that follow, and in part will be apparent from the description, or may be learned by practice of the embodiments. The objectives and other advantages of the embodiments will be realized and attained by the structure particularly pointed out in the written description, claims and the appended drawings.

BRIEF DESCRIPTION OF THE DRAWINGS

The novel features of the embodiments are set forth with particularity in the appended claims. A better understanding of the features and advantages will be facilitated by referring to the following detailed description that sets forth illustrative, as well as to the accompanying drawings, in which like numerals refer to like parts throughout the different views. Like parts, however, do not always have like reference numerals. Further, the drawings are not drawn to scale, and emphasis has instead been placed on illustrating the principles of the embodiments. All illustrations are intended to convey concepts, where relative sizes, shapes, and other detailed attributes may be illustrated schematically rather than depicted literally or precisely.

FIG. 6A1 shows corneal profile data for the coordinate system and image of FIG. 6A;

FIG. 6A2 shows corneal thickness profile data for the coordinate system and images of FIGS. 6A and 6A1;

FIG. 6A3 shows corneal thickness profile maps for the coordinate system and images of FIGS. 6A, 6A1 and 6A2;

FIG. 6C1 shows corneal profile data for the coordinate system and image of FIG. 6C;

FIG. 6C2 shows corneal thickness profile data for the coordinate system and images of FIGS. 6C and 6C1;

FIG. 6C3 shows corneal thickness profile maps for the coordinate system and images of FIGS. 6C, 6C1 and 6C2;

DETAILED DESCRIPTION OF THE INVENTION

Figure 1:
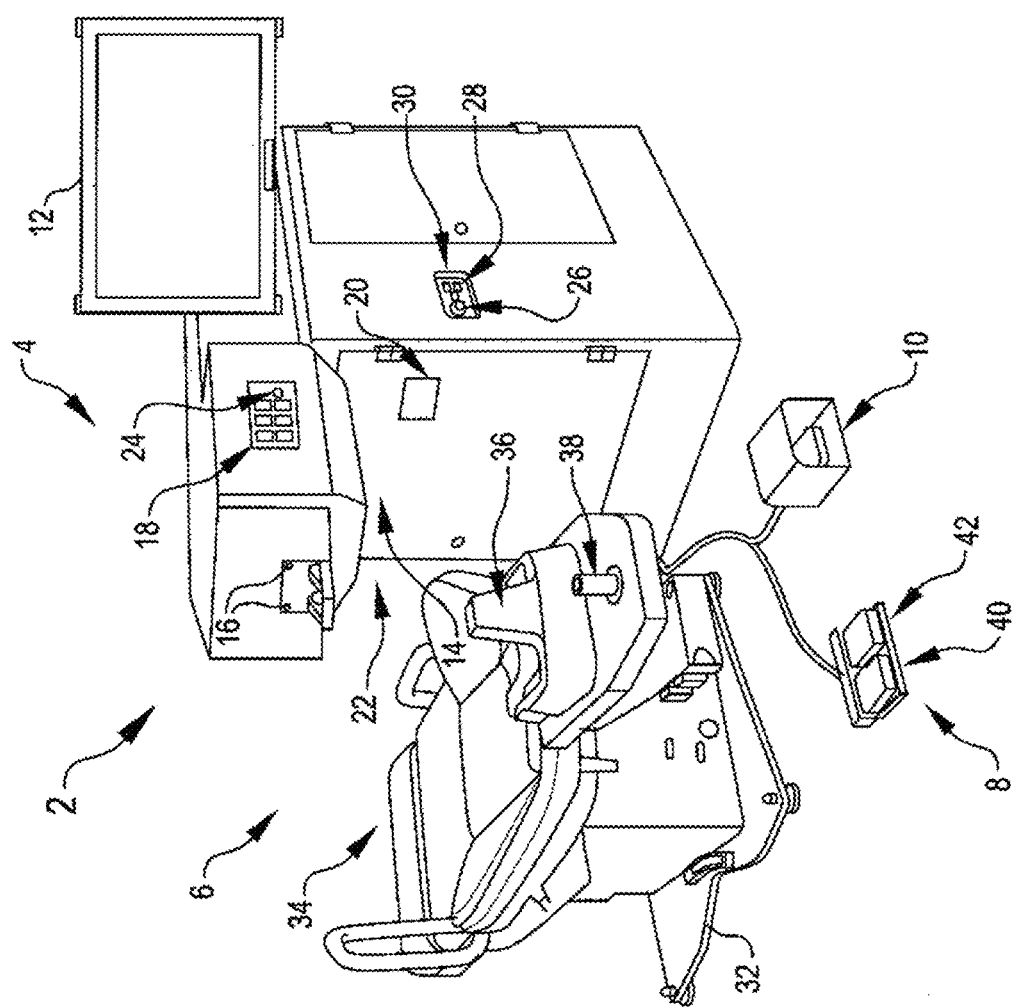
FIG. 1 shows a perspective view showing a laser eye surgery system, in accordance with many embodiments.

Methods and systems related to ophthalmic measurements and laser eye surgery are disclosed. In many embodiments, a laser is used to form precise incisions in the cornea, in the lens capsule, and/or in the crystalline lens nucleus. Although specific reference is made to tissue resection for laser eye surgery, embodiments as described herein can be used in one or more of many ways with many surgical procedures and devices, such as orthopedic surgery, robotic surgery and microkeratomes.

The embodiments as described herein are particularly well suited for mapping the index of refraction with a first beam having first one or more wavelengths of light. The mapped index of refraction can be used to determine the physical location of the tissue structure, in response to a mapped index of refraction along the measurement beam path extending to the tissue structure, for example.

A laser may be used to form precise incisions in the cornea, in the lens capsule, and/or in the crystalline lens nucleus, for example. The embodiments as described herein can be particularly well suited for increasing the accuracy of the cutting of the material such as tissue, for example. For example, the mapped index of refraction can be used to determine the location of one or more components of the laser system such as a lens and movable mirrors in order to more accurately place the laser beam focus and tissue incisions. In many embodiments, tissue structures are mapped with a beam of a measurement system such as a tomography system and the index of refraction of the tissue is mapped with the focused measurement beam as described herein. The tissue structures mapped with the measurement beam can be adjusted in response to the mapped indices of refraction from the focused measurement beam in order to more accurately determine the physical locations of the tissue structures.

The physical locations and dimensions of the tissue structures of the eye and the mapped indices of refraction can be used to more accurately determine the positions of the laser system components. For example, the laser beam incision profile of the tissue of the eye can be determined in response to physical locations of tissue structures or the locations of the structures from tomography images, and combinations thereof. In many embodiments, the mapped indices of refraction determined with the focused measurement beam having first one or more wavelengths are adjusted in response to an index of refraction of the laser treatment beam having second one or more wavelengths in order to provide mapping of the index of refraction for the treatment beam. The range of the first one or more wavelengths can overlap with the range of the second one or more wavelengths such that the wavelengths are similar, or have non-overlapping ranges such that the first one or more wavelengths differs from the second one or more wavelengths. The mapped index of refraction of the treatment beam can be combined with one or more of the physical locations and dimensions of the tissue structures, the targeted incision profile, or the mapped index of refraction of the focused measurement beam, in order to determine the positions of the mirrors and lenses of the laser treatment system to place the laser beam incisions at the targeted locations of the eye.

In many embodiments, the index of refraction of the treatment beam can be determined by adjusting the measured index of refraction of the measurement beam to correct for differences in the indices of refraction of the treatment beam and measurement beam. Alternatively or in combination a baseline index of refraction of the treatment beam can be adjusted in response to the index of refraction measured with the measurement beam. In many embodiments, a baseline index of refraction is adjusted in response to the measured index of refraction. The baseline index of refraction may comprise an index of refraction of a structure of the eye. While the index of refraction of tissue such as eye can vary with wavelength as described herein, approximate baseline values include: aqueous humor 1.33; cornea 1.38; vitreous humor 1.34; and lens 1.36 to 1.41, in which the index of the lens can differ for the capsule, the cortex and the nucleus, for example. The baseline phase indices of refraction of water and saline can be about 1.325 for the ultrafast laser at 1030 nm and about 1.328 for the OCT system at 830 nm, and this proportional difference can be used to determine the index of refraction of the treatment beam in response to the index of refraction measured with the measurement beam, for example. The group refractive index of 1.339 differs on the order of 1% for the OCT beam wavelength and spectral bandwidth. Many embodiments herein provide methods and apparatus for determining the indices of refraction, the phase indices of refraction, and group indices of refraction of the tissues of the eye for the wavelengths of the measurement and treatment systems as described herein.

The embodiments disclosed herein are well suited for combination with prior laser surgery systems, such as the CATALYS Precision Laser System available from Abbott Medical Optics Inc., and similar systems. Such systems can be modified in accordance with the teachings disclosed herein and to more accurately measure and treat the eye.

As used herein like characters such as reference numerals and letters described like elements.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

The processor system may comprise tangible medium embodying instructions of a computer program to perform one or more of the method steps as described herein.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) for example, to enable export of treatment reports to a data storage device. The treatments reports stored on the data storage device can then be accessed at a later time for any suitable purpose such as, for example, printing from an external computer in the case where the user without access to network based printing.

Figure 2:
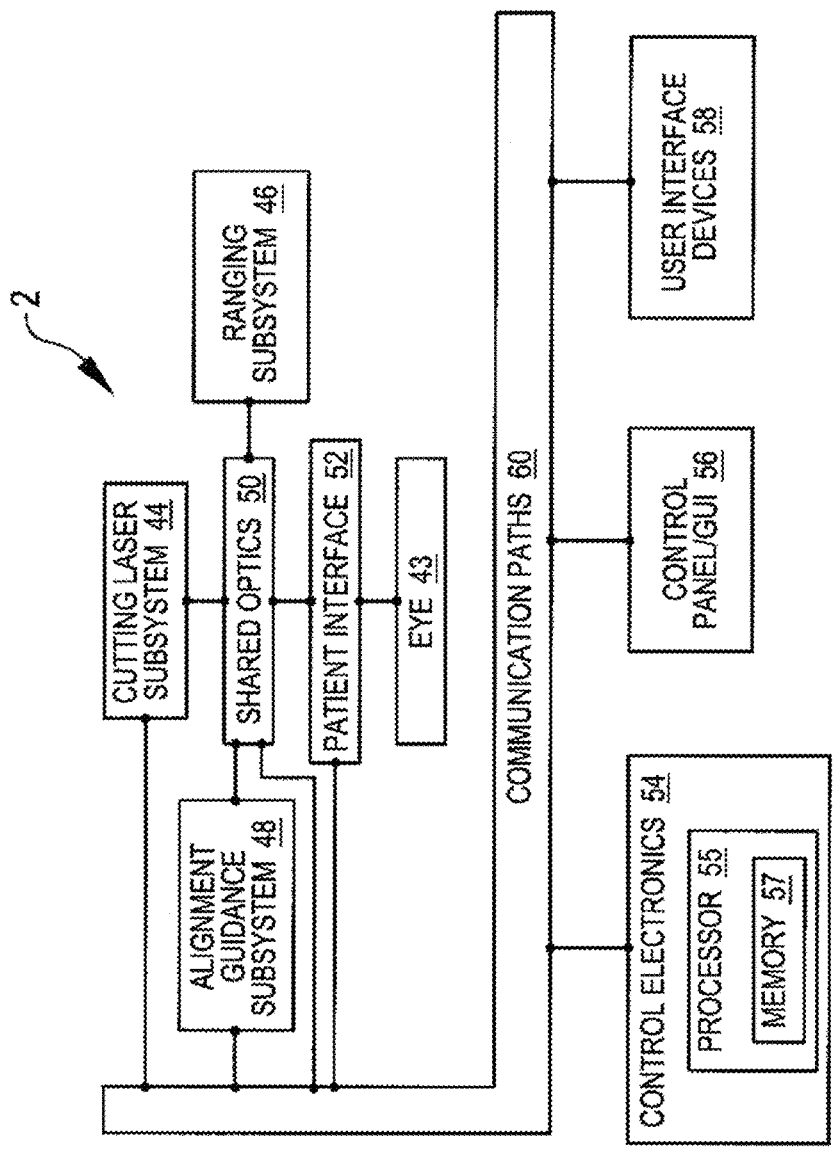
FIG. 2 shows a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea 43C, a lens 43L and an iris 43I. The iris 43I defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately 10-13 seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 52 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
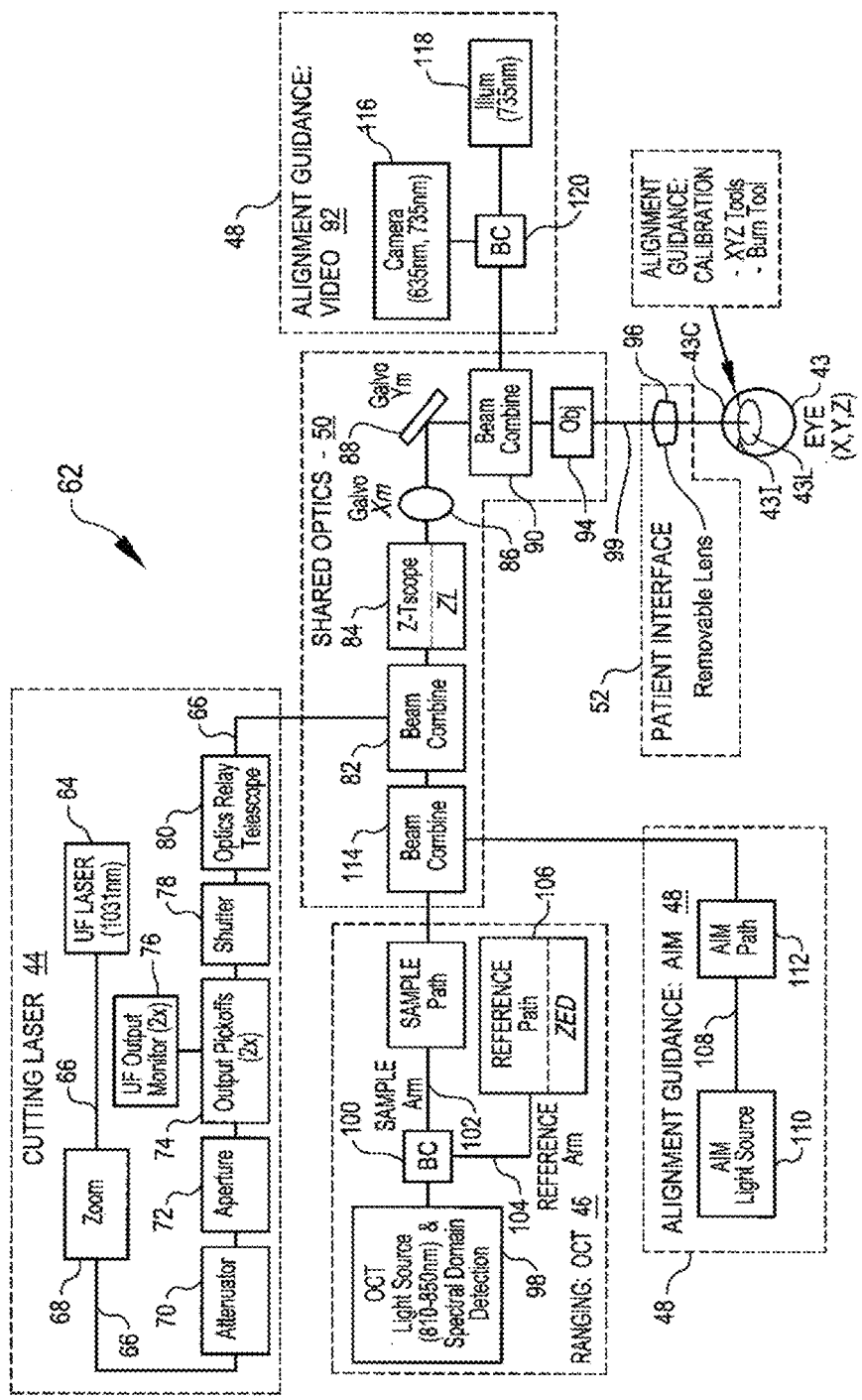
FIG. 3A shows a simplified block diagram illustrating the configuration of an optical assembly of a laser eye surgery system, in accordance with many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, and Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian a focal telescope that relays an image of the aperture position to a conjugate position near to the xy galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66.

The X-scan device 86 is controlled by the control electronics 54, and can include suitable components, such as a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structures of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3 includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber, and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc., are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
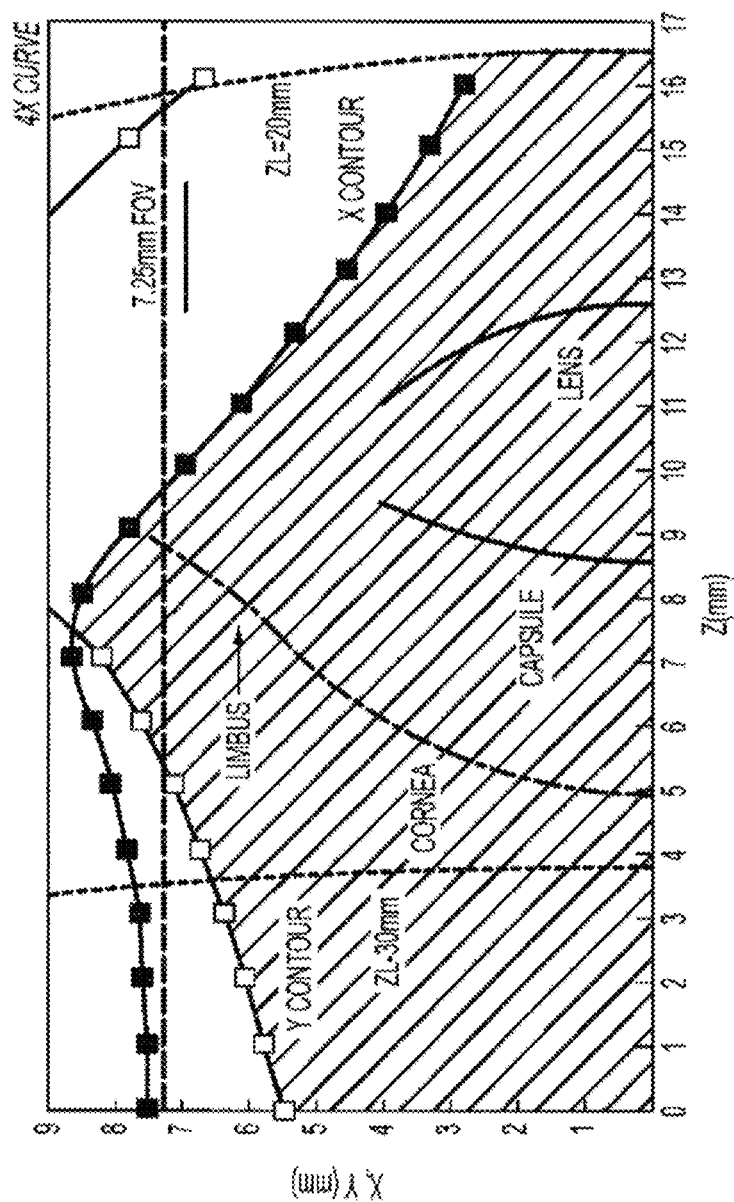
FIG. 3B shows a mapped treatment region of the eye comprising the cornea, the posterior capsule, and the limbus, in accordance with many embodiments.

FIG. 3B shows a mapped treatment region of the eye comprising the cornea, the posterior capsule, and the limbus. The treatment region can be mapped with computer modeling, for example ray tracing and phased based optical modeling to incorporate factors such as laser beam quality, pulse width, system transmission, numerical aperture, polarization, aberration correction, and alignment. The treatment volume is shown extending along the Z-axis from the posterior surface of the optically transmissive structure of the patient interface a distance of over 15 mm, such that the treatment volume includes the cornea, and the lens in which the treatment volume of the lens includes the anterior capsule, the posterior capsule, the nucleus and the cortex. The treatment volume extends laterally from the center of the cornea to beyond the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of predicted optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planner shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume may optionally be adjusted with mapping based on measurements of a constructed system as described herein.

Figure 4A:
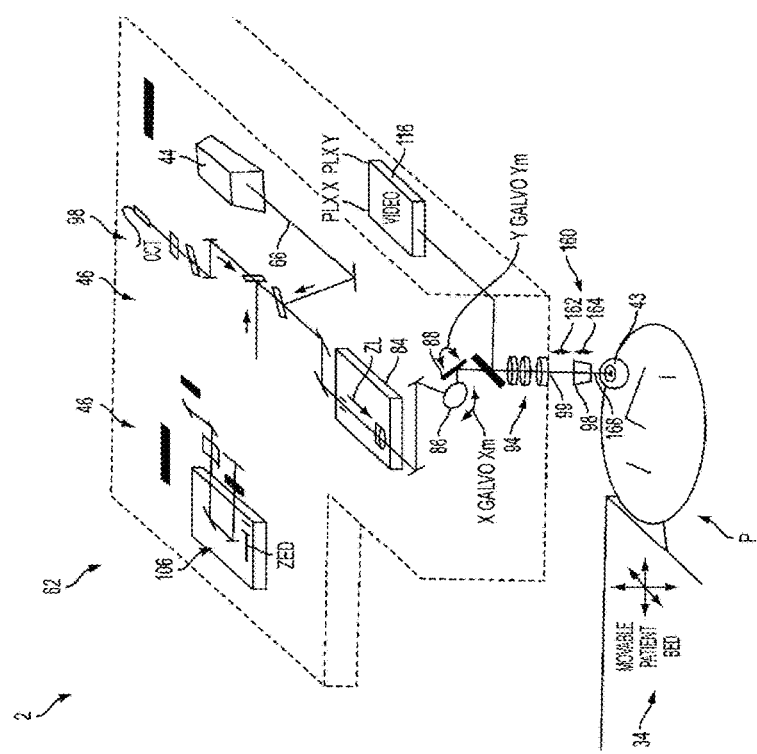
FIG. 4A shows correspondence among movable and sensor components of the laser delivery system, in accordance with many embodiments.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount $X_m$, and the Y galvo mirror 88 capable of moving an angular amount $Y_m$. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

Figure 4B:
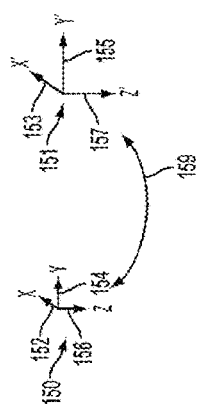
FIG. 4B shows mapping of coordinate references from an eye space coordinate reference system to a machine coordinate reference system, in accordance with many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example. In many embodiments, the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In the context of cataract surgery, the system may be configured to perform capsulotomy and lens fragmentation incisions as disclosed for instance, in U.S. Pat. No. 8,500,724, entitled "Method and Apparatus for Patterned Plasma-mediated Laser Trephination of the Lens Capsule and Three-dimensional Phaco-segmentation," which is incorporated herein by reference in its entirety. The system may likewise be configured to perform one or more corneal incisions, including without limitation one or more cataract incisions, sideport incisions or relaxing incisions, as disclosed for instance in U.S. Patent Publ. 2008/0281303, entitled "Method and Apparatus for Creating Ocular Surgical and Relaxing Incision," the entirety of which is incorporated herein by reference in its entirety.

The laser surgery system according to the present invention preferably includes a corneal topography subsystem. The corneal topography subsystem general refers to those portions of the laser surgery system which operate cooperatively to measure the anterior corneal topography of the eye and/or the posterior corneal topography to provide information regarding the anterior corneal surface and/or the posterior corneal surface. The corneal surface information, either anterior corneal surface information and/or posterior corneal surface information, preferably relates to at least one property of the selected corneal surface affecting the refractive characteristics of the eye.

In many embodiments, the method for obtaining corneal topography measurements of the patient's eye comprises coupling a corneal topography measurement structure to a patient interface structure to place the topography measurement structure in front of the eye. The eye may be measured with the topography measurement structure and the patient interface away from the eye. The corneal topography measurement structure is decoupled from the patient interface structure. The patient interface structure is coupled to a component of the patient interface in order to contact the eye. In some embodiments, an astigmatism axis of the eye is determined in response to the measurement of the eye with the corneal topography structure removably coupled to the patient interface. In other embodiments, the topography measurement structure is permanently affixed to the laser surgical system.

In another aspect, embodiments provide an apparatus to measure an eye. The apparatus comprises a patient interface. A topography measurement structure is configured to couple to the patient interface to measure the eye without contacting the eye.

In many embodiments, corneal surface information may include an axis, meridian or structure that a physician or other user may wish to visually identify without the aid of a user interface, such as a display, and may desire visual markers (identifiers) to be present near the optical tissue of the eye being treated. In many embodiments, the axis, meridian or structure of the eye to be visualized may be marked with fiducial mark incisions on the periphery of the eye as described herein. The fiducial mark incisions preferably provide a visible marker of the selected axis so that its location and orientation can be accurately determined by visual inspection. Visual inspection includes visual inspection under magnification, such as by a microscope.

For instance, in an astigmatic eye, a physician or other user may wish to visualize the steepest meridian of the cornea for alignment of a toric IOL within the eye during cataract surgery. The steepest meridian may be identified by a corneal topographer. Radial fiducial mark incisions disposed along the steep axis of the cornea of the patient's eye are referred to herein as toric fiducial mark incisions (or alternatively, "toric fiducial marks"). The placement of the toric fiducial mark incisions permits a treating physician to align a toric IOL with the steep axis of the eye during cataract surgery. Advantages of the toric fiducial marks include the reduction in manual error of placing a mark, the laser marks are visible for a longer duration and the number of measurements a patient-user need perform is minimized.

The fiducial mark incisions generally comprise two small, radial incisions in the cornea disposed at the periphery of the eye along the selected axis and centered on one of the limbus, iris or scanned capsule. The marks are preferably disposed 180 degrees about the center of the axis and more preferably are diametrically opposed. Fiducial mark incisions may be generated as two line segments defined by an intersection of a horizontal line passing through a center with a horizontal ring having an inner diameter defined by an optical zone and a thickness length and a width. These two line segments having a length (in microns) that are x-y projections of fiducial marks to be placed in the cornea, preferably intrastromally and outside the optical zone of the eye. Other shapes and placement of the fiducial marks are shown herein in FIGS. 15-19 and the associated text and are described in U.S. Pat. No. 14/255,430, filed Apr. 17, 2014, entitled, "LASER FIDUCIALS FOR AXIS ALIGNMENT IN CATARACT SURGERY,"

The fiducial mark incisions generally do not alter the optical properties of the cornea. Preferably, the length of the incision is less than 5 mm, preferably less than 2.5 mm and more preferably 1.5 mm or less. It has been found that an incision length of 1.5 mm or less provides an optically visible incision that heals rapidly and does not alter the optical properties with a suitable margin of error. The pulse energy used in the producing the fiducial mark incisions is generally lower than what is used for capsulorhexis or capsulotomy incisions, limbal relaxing incisions and lens fragmentation, and is preferably between 0.5 microjoules and 8 microjoules, more preferably between 3 microjoules and 10 microjoules and more preferably between 4 microjoules and 6 microjoules.

The axis, meridian or structure for which visual identification is desired is preferably measured by corneal topography or tomography. The corneal topography measurement structure may comprise an external illumination structure such as a ring or disk shaped illuminator that illuminates the eye to form a ring or disk shaped virtual image of the illumination structure, and the astigmatic axis of the cornea and the steepest meridian are determined based on measurements of the virtual image of the eye. The external illuminator can be configured to couple to the patient interface for measurement of the eye and removed when the eye has been docked to the patient interface.

After measurement by the corneal topographer, a patient interface is generally used to restrain the position of the patient's eye relative to the system. Between measurement of corneal topography and the placement of the patient interface, the patient's eye may have moved resulting in the movement of the axis, meridian or structure for which visual identification is desired. In many embodiments, iris registration is used to determine a cyclotorsional angle of the eye when the user interface is attached relative to its non-contact position during corneal topography measurements. For instance, a first image of the iris is obtained with a first camera prior to the patient interface contacting the eye, and a second image of the iris is obtained when the patient interface contacts the eye. The first image and the second image can be registered in one or more of many ways, and the processor can be configured with instructions to determine the cyclotorsional angle of the eye such as by image matching algorithm or a pattern recognition algorithm. The processor comprising the instructions of the algorithm can thus be configured to identify a pattern of the first image in relation to an axis of the eye as described herein and to identify the location of the pattern in the second image in order to determine the cyclotorsional angle of the eye, for example. The cyclotorsional angle of the eye can then be used to determine the position of the eye with patient interface is attached, including the axis, meridian or structure for which visual identification is desired.

Thereafter, the fiducial mark incisions may be accurately incised along the axis, meridian or structure with the patient interface secured to the patients eye. Additional incisions by the laser surgical system may include one or more of a capsulotomy, limbal relaxing incisions, and lens fragmentation and/or segmentation patterns. After incision of the relevant tissues is completed, the patient interface may be removed, and the lens may subsequently be removed.

Figure 5A:
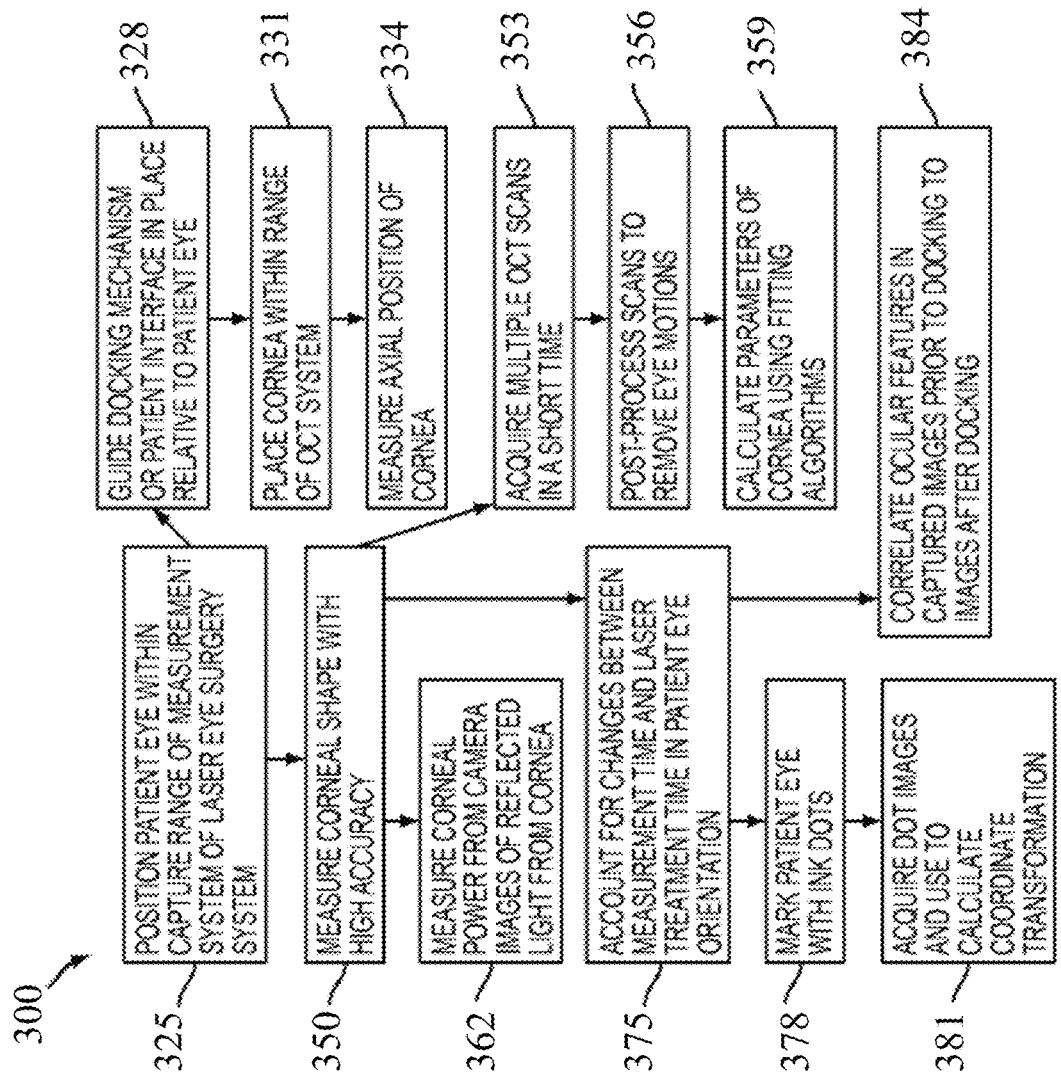
FIG. 5A shows a flow chart of a method for mapping the eye, in accordance with many embodiments.

FIG. 5A shows a flow chart of a method 300 for providing accurate and distortion-free corneal topography measurement and subsequent integration with the laser treatment, in accordance with embodiments. The method 300 comprises the following main steps. In a step 325, the patient's eye is positioned within the capture range of the measurement system of the laser eye surgery system 2 or 2A described herein. In a step 350, the measurement system is used to measure corneal shape with high accuracy. Such a measurement system may comprise the ranging subsystem 46 described above. In a step 375, any changes in the patient eye orientation that may occur between the measurement time and the laser treatment time is accounted for.

Positioning step 325: In the step 325, the patient's eye is positioned within the capture range of the measurement system of the laser eye surgery system as described herein, such as shown in FIGS. 2 and 3A, for example. Positioning of the patient for laser surgery is typically enabled by motion of the patient bed 34 or by motion of the laser system 2. Typically, the operator has manual control of the lateral and axial position, guiding the docking mechanism or patient interface 52 into place in a step 328. In the absence of a docking mechanism, an operator means for guiding the motion so that the eye, and specifically the cornea, is placed within the operative range of the measurement system may be provided. This can be accomplished with the use of subsystems of the laser system 2 or 2a described herein such as alignment guidance system 48 of laser system 2 or imaging subsystem 346 of laser system 2a. Initial patient position can be guided by a video camera, guiding the eye into lateral position by centering the video image, and into axial position by focusing the image. At this point, the cornea is placed within the capture range of the OCT system of the ranging subsystem 46 or imaging subsystem 546, typically X mm to Y mm axially, in a step 331. The OCT system can be used to measure the axial position of the cornea in a step 334, and a suitable display provides the operator guidance for final, accurate positioning. Alternatively, a visual imaging system such as a camera, a camera coupled to a microscope which may share optics with the laser system 2 or 2a, a CCD, among others may be used instead of the OCT system to facilitate the positioning step 325.

Since the video and OCT systems are typically configured to operate with the docking system, which often has additional optical elements and liquid medium in the optics path, the focusing algorithms of the laser system may be adjusted to account for operation without the docking mechanism optics and interface medium.

Measurement step 350: In the step 350, the measurement system is used to measure corneal shape with high accuracy. The laser system 2 or 2A comprises a subsystem for mapping the ocular surfaces that are being treated such as the ranging subsystem 46 having an OCT system described herein or the imaging subsystem 546. As described below, the imaging subsystem 546 may apply other modalities for mapping the ocular surfaces such as Placido imaging, Hartmann-shack wavefront sensing, confocal tomography, low coherence reflectometry, among others. The measurement step 350 can be performed once the eye is positioned correctly in the step 325 above. A fixation light can optionally be introduced to help the patient keep the eye pointed at a fixed angle. If the measurement data capture is sufficiently fast, for example, on the order of one second, a fixation light may not be necessary. In a step 353 of measurement 550, multiple OCT or other scans of the cornea surfaces can be acquired in a short time. Multiple scans can increase the confidence of obtaining good data. In a step 356, post-processing of the scans can remove potential eye motion and further improve the measurement accuracy. In a step 362 of measurement step 350, corneal power can be measured from camera images of reflected light from the cornea.

Once the cornea surfaces have been mapped, polynomial, or other fitting algorithms can be used to calculate commonly used parameters of the cornea in a step 359. Commonly used parameters include the optical power of the cornea, astigmatic axis angle, and astigmatism magnitude.

Coordinate system transfer step 375: In the step 375, any changes in the patient eye orientation that may occur between the measurement time and the laser treatment time is accounted for. Often times, it is probable that when the patient eye is docked for treatment such as with the suction ring of the patient interface 52, the eye, including its various anatomical features, will change its position relative to the laser system coordinates. This change can be a result of patient head movement, eye movement, or because of force applied during docking. In some cases, the refractive properties of the air or any liquid over the eye can distort the images of the eye. For example, the suction ring of the patient interface 52 may be filled with one or more of a solution, saline, or a viscoelastic fluid. It can be helpful to transform the corneal measurements, like the astigmatic axis angle, to a new coordinate system to account for any movement and distortion. Several means for accomplishing this are provided.

In some embodiments, the operator can mark the patient eye prior to the measurement with ink dots that are typically positioned diametrically across on the periphery of the cornea in a step 378. These dots can be acquired by the imaging camera after docking for treatment and used for calculating the coordinate transformation in a step 381.

In other embodiments, ocular features that are visible in the video images, or the OCT or other scans, taken during the measurement step are used. These features are correlated to the images taken after docking for treatment in a step 384. This correlation can be done by digital image processing algorithms, or manually by the operator. When done manually, the operator is presented by overlapped images (measurement and treatment steps) on the control screen, and the images are manually manipulated in translation and rotation until they are visibly matched. The image manipulation data can be detected by the display software and used for the coordinate transform.

Although the above steps show method 500 of providing accurate and distortion-free corneal topography measurement and subsequent integration with the laser treatment in accordance with many embodiments, a person of ordinary skill in the art will recognize many variations based on the teaching described herein. The steps may be completed in a different order. Steps may be added or deleted. For example, the shape of the cornea may be measures before, during, or after docking for treatment such as with a suction ring of the patient interface 52. Many of the steps may be repeated as often as beneficial to the method.

One or more of the steps of the method 500 may be performed with the circuitry as described herein, for example, one or more the processor or logic circuitry such as the programmable array logic for field programmable gate arrays. The circuitry may be programmed to provide one or more of the steps of method 500, and the program may comprise program instructions stored on a computer readable memory or programmed steps of the logic circuitry such as the programmable array logic or the field programmable gate array, for example.

Figure 5B:
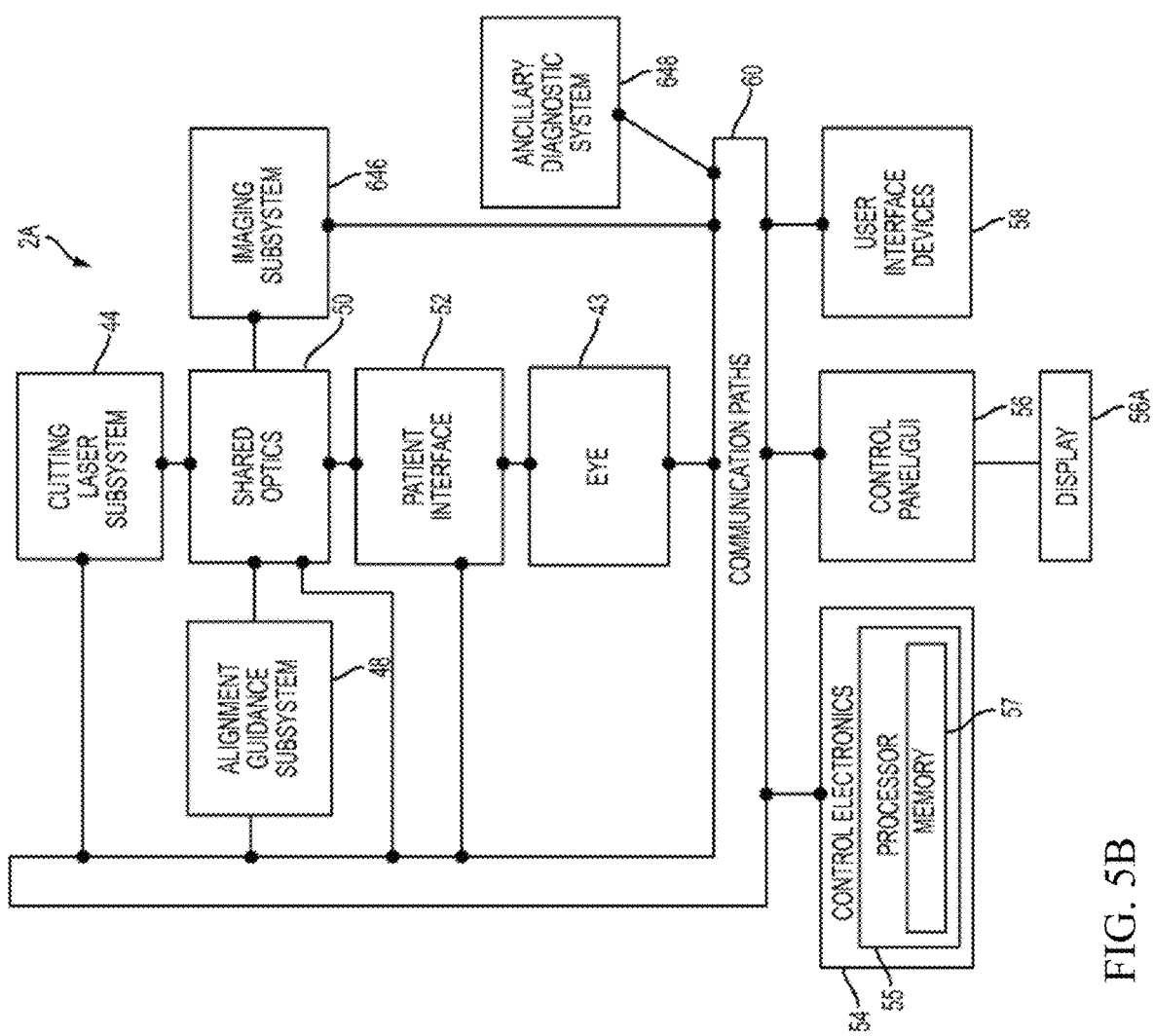
FIG. 5B shows a simplified block diagram showing a top level view of the configuration of a laser eye surgery system which can perform the method of FIG. 5A, in accordance with many embodiments.

FIG. 5B shows a laser eye surgery 2A similar to system 2 of FIG. 2 in accordance with embodiments. The laser eye surgery system 2 is similar to the laser eye surgery system 2 as described herein and comprises many of the same components. In particular, the laser eye surgery system 2A comprises an imaging subsystem 646 which may be used to visualize and image the eye 43, and the control panel/GUI 56 comprises a display 56A. The laser eye surgery system 2A may be configured to couple to a separate and distinct ancillary diagnostic system 648. For the laser eye surgery system 2, the OCT system of the ranging subsystem 46 may be used to position the patient eye in the step 325 and/or to measure the shape of the cornea in the step 350. For the laser eye surgery system 2A, the ancillary diagnostic system 648 is used to measure the shape of the cornea in the step 350. The ancillary diagnostic system 648 may apply any number of modalities to measure the shape of the eye including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye. The shape of the cornea can be measured before, during, or after the patient interface 52 is docked with the eye of the patient. The shape of the cornea may be measured using the ancillary diagnostic system 648 while the ancillary diagnostic system 648 is separate from the laser eye surgery system 2A, such as by being in a different room. Images captured by the ranging subsystem 46 of the laser eye surgery system 2 or the imaging subsystem 546 of the laser eye surgery system 2A and the ancillary diagnostic system 548 may be displayed with a display of the control panel/GUI 56 of the laser eye surgery system 2 or the display 56A of the laser eye surgery system 2A, respectively. The control panel/GUI 56 may also be used to modify, distort, or transform any of the displayed images.

FIGS. 8A-8D show a corneal topography measurement structure configured to couple to a patient interface 52 as described herein to measure the eye prior to the eye contacting the patient interface. The topography measurement structure may comprise one or more of a ring or other structure for a keratometry reading of the eye, a Placido disc topography of the eye, a reflection of a plurality of points from the cornea topography of the eye, a grid reflected from the cornea of the eye topography. In many embodiments, the measurement structure comprises a Placido disc structure configured to couple to a component of the patient interface, for example. The topography measurement structure can be illuminated, for example, so as to form a virtual image of the measurement structure when reflected from the cornea. One illumination strategy could make use of the internal existing illuminator of the system itself. Alternatively or in combination, the topography structure may comprise a ring illuminator either mounted to the patient interface or to the structure of the laser system.

In many embodiments, topography measurement structure is back illuminated with light from the laser system to illuminate the eye with the topography measurement structure. Alternatively or in combination the topography measurement structure may comprise a plurality of light sources such as light emitting diodes to illuminate the eye with the topography measurement structure.

Figure 8A:
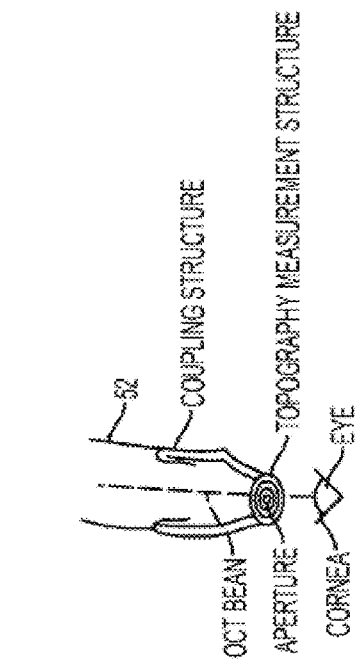
FIG. 8A shows a topography measurement structure configured to couple to a patient interface to measure the eye prior to the eye contacting the patient interface, in accordance with embodiments.
Figure 8B:
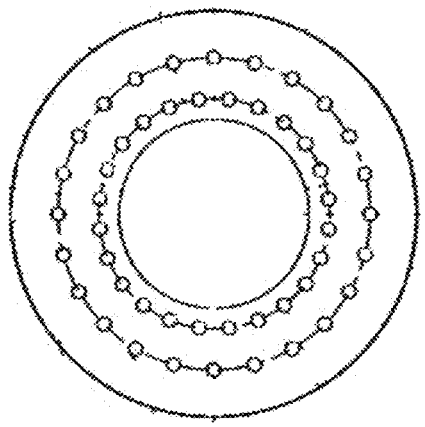
FIG. 8B shows components of the patient interface and the topography measurement structure configured to couple to the patient interface, in accordance with embodiments.
Figure 8C:
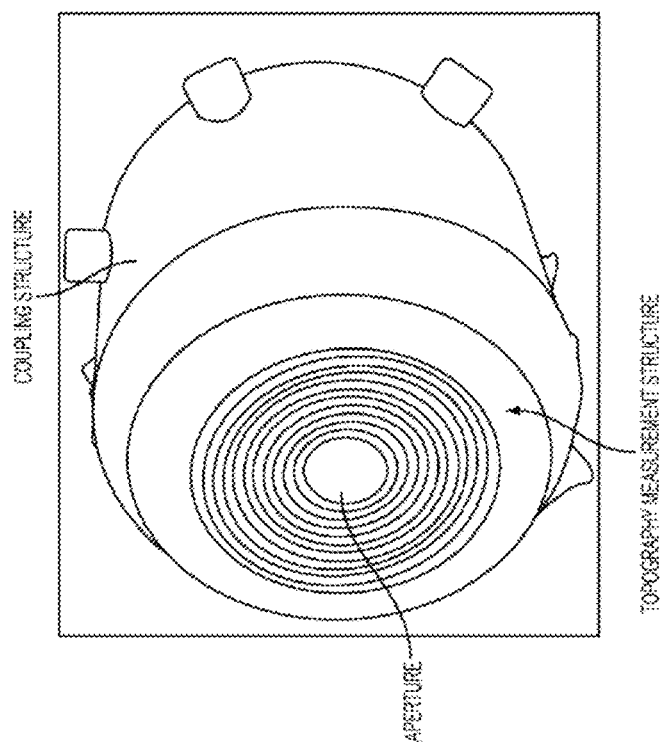
FIG. 8C shows a perspective view of the interface end of the topography measurement structure.
Figure 8D:
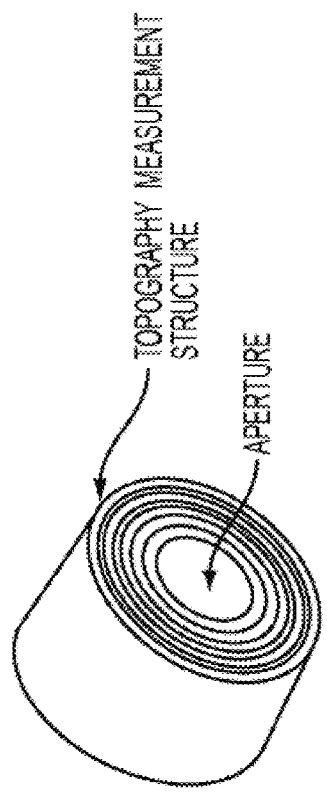
FIG. 8D shows an end face of the topography measurement structure showing the circular opening and the aperture.

FIG. 8B shows the topography measurement structure removable coupled to the patient interface to position the topography measurement structure in relation to the eye when the patient has been placed on the support of the laser eye surgery system as described herein. The OCT measurement beam can be used to position the eye. This use of the OCT measurement beam may be particularly important to achieve absolute curvature readings of the Placido system as the diameter of the reflected Placido rings may depend not only on the curvature of the cornea but also from the distance of the ring illuminator and the cornea. OCT can help to minimize these variations. Additionally, this measurement information can also be used to actively track position the patient's chair and move the eye into the correct or desired position. Additionally, the OCT system and optionally also the camera can be used to locate the actual position of the Placido ring in relation to the system to enable high precision measurements. Alternatively or in combination, the focus of the video camera as describe herein can be used to position the eye for measurement. When the topography of the patient has been measured and the axis determined, for example, the topography measurement system can be decoupled from the patient interface structure and the patient interface coupled to the eye as described herein.

The Placido disk illuminator can be constructed in many different ways. Having a clear aperture in the center of the ring structure to allow the video system to be used as is may be particularly important. Other embodiments may comprise a combination of different engineered diffusers and masks which can be optimized on the diffusing angle used to the detection of the rings from the cornea. Or, if polarized light is used, a combination of quarter wave plate or depolarizer and diffuser with ring apertures can be used. For full utilization, the light illuminated on the blocked rings can make the blocked rings act as reflecting wedges so the light is fully utilized. In such cases, an angle which enables total reflection may be helpful. Utilizing a combination of a strong negative lens and the Placido disk illuminator can also increase the light intensity of the outer rings for better contrast.

In many embodiments, the topography measurement structure comprises an external illumination structure such as a ring illuminator illuminates the eye to form a ring shaped virtual image of the illumination structure, and the astigmatic axis of the eye determined based on measurements of the virtual image of the eye as described herein. The external illuminator can be configured to couple to the patient interface for measurement of the eye and removed when the eye has been docked to the patient interface. Alternatively, the external illuminator may comprise a substantially fixed structure that remains fixed to the laser system throughout a plurality of procedures.

The corneal topography data and thickness data can be combined in one or more of many ways. For example, the corneal topography data can be used to determine the shape profile of the anterior corneal surface, and the corneal thickness profile data can be fit to the anterior corneal surface profile in order to determine the profile of the posterior surface, for example. In many embodiments, the anterior corneal surface profile is measured and determined without the patient interface contacting the eye, and the corneal thickness profile is measured and determined when the patient interface contacts the eye. The corneal surface profile data measured without contacting the eye can be combined with the corneal thickness profile data measured with the patient interface contacting the eye, and the location of refractive incisions determined in response to both profiles, for example.

FIG. 8B shows components of the patient interface and the topography measurement structure configured to couple to the patient interface.

In some embodiments, corneal thickness maps may be generated in order to determine posterior corneal surface information.

Figure 6C:
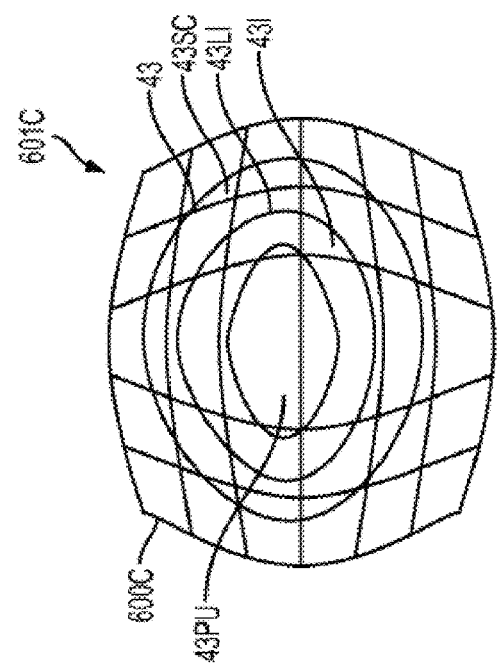
FIG. 6C shows a distorted coordinate system overlaid on the eye image of FIG. 6B to account for distortion due coupling of the eye to a patient interface as well as liquid in the patient interface disposed over the eye, in accordance with many embodiments.
Figure 6A:
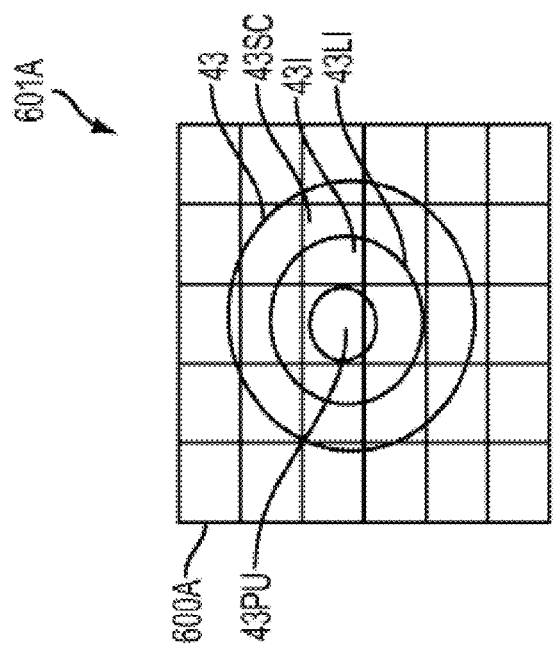
FIG. 6A shows a coordinate system overlaid on an image of the eye, in accordance with many embodiments.
Figure 6B:
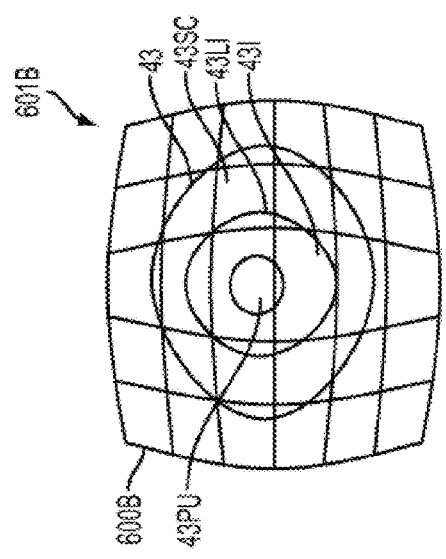
FIG. 6B shows a distorted coordinate system overlaid on the eye image of FIG. 6A to account for distortions due coupling of the eye to a patient interface, in accordance with many embodiments.

FIGS. 6A to 6C show images of the eye which may be displayed for example in the display 56A of the laser eye surgery system 2A or the display of the laser eye surgery system 2, for example. The images shown illustrate distortion which may occur and the distortion may not be to scale and is provided for illustration purposes in accordance with embodiments.

FIG. 6A shows a coordinate system 600A overlaid on an image 601A of an eye EY. The image 601A of the eye 43 shows various anatomical features including the sclera 43SC, the limbus 43LI, the iris 43I, and the pupil 43PU. Similar images and biometric information can be obtained with similar maps. In many embodiments, this image 601A can be captured by the imaging subsystem 546 of the laser eye surgery system 2A. The image 601A is captured prior to coupling the eye with a suction ring of the patient interface 52 of the laser eye surgery system 2. The image 601A may most accurately represent the positions of the various tissue structures of the eye 43. The image 601A may comprise one or more of many images or measurements as described herein. A person of ordinary skill in the art will recognize that the pupil seen through the cornea/air interface comprises a virtual pupil of the eye. Although the shape and optical power of the cornea may provide distortion and magnification of the pupil and iris, a person of ordinary skill in the art can correct this distortion and magnification based on the teaching described herein and in accordance with embodiments as appropriate. For example, the virtual image of the pupil can be transformed to an eye space coordinate system 150 as described herein.

The structures shown in coordinate system 600A can be transformed to the coordinate reference system 150 of eye 2 in one or more of many ways. For example, the tissue structures shown in the image such as the limbus and the iris can be identified, and the transform to the eye coordinate reference system 150 determined based on the location of the tissue structure and depth and location in relation to correspondence optical tissue surfaces such as the surface of the cornea. The locations of the tissue structures identified in the image 601 can be determined and mapped to eye coordinate reference system 150 or to one or more coordinate reference systems as described herein.

In many embodiments, iris registration is used to determine a cyclotorsional angle of the eye. A first image of the iris can be obtained with a first camera prior to the patient interface contacting the eye, and a second image of the iris can be obtained when the patient interface contacts the eye. The first camera image of the iris can be registered with the second camera image of the iris of the patient in order to determine the cyclo torsional angle of the eye as described herein. In many embodiments, the first non-contact image of the eye comprises an image of the iris wherein the cornea of the eye magnifies and may distort the virtual image of the iris seen with the camera, and the second contact image of the eye comprises an image of the eye measured when the patient interface contacts the eye. The first image and the second image can be registered in one or more of many ways, and the processor can be configured with instructions to determine the cyclotorsional angle of the eye with instructions of an algorithm such as one or more of an image matching algorithm or a pattern recognition algorithm, for example. The processor comprising the instructions of the algorithm can be configured to identify a pattern of the first image in relation to an axis of the eye as described herein and to identify the location of the pattern in the second image in order to determine the cyclotorsional angle of the eye, for example.

In many embodiments, ray tracing through the full thickness corneal profile map can be used to correct distortions of the cornea, such as one or more of distortions of the anterior corneal surface of the posterior corneal surface. For example, when the eye has been docked and the fluid of the patient interface contacts the eye, distortions of the posterior surface of the eye can influence light rays travelling through the cornea, and distortions of images of tissue structure posterior to the posterior surface of the cornea can be corrected in response to ray tracing. The ray tracing can be performed by a person of ordinary skill in the art using Snell's law and the index of refraction of the cornea and contacting material such as air, interface fluid, or aqueous humor, for example. Alternatively or in combination, distortions of the anterior corneal surface and the corresponding distortion of images measured through the cornea can be corrected with ray tracing, for example when the cornea is exposed to air. While distortions of the anterior corneal surface can be corrected in a manner similar to the posterior surface with ray tracing, work in relation to embodiments suggests that coupling the eye to the patient interface with a fluid contacting the patient interface and having an index of refraction similar to the cornea can decrease the effect of distortions of the anterior corneal surface. Based on the teachings disclosed herein, a person of ordinary skill in the art can determine and correct for distortions of images of the eye related to corneal distortions with ray tracing and corneal profile maps as described herein, for example.

In many embodiments one or more of the first image or the second image is adjusted in response to distortion of the one or more of the first image or the second image. The distortion can be related to the index of refraction viscous fluid into the patient interface that affects the optical properties of the image of the eye, or the distortion of the optical delivery system, and combinations thereof. In many embodiments, the distortion of the cornea can be determined in response to a thickness profile of the cornea, and aberrations of the image introduced by the thickness profile of the cornea corrected.

FIG. 6A1 shows corneal profile data 610A of cornea 43C for the coordinate system and image of FIG. 6A. The corneal profile data 610A comprises a plurality of corneal profiles from the tomography system taken with the patient interface away from the eye as in FIG. 6A. The plurality of corneal profiles comprises a first corneal profile 612A, a second corneal profile 614A and a third corneal profile 616A. Additional corneal profiles can be taken. The cornea profiles can be obtained with tomography scans along a plane for example, and detection of the corneal surface. The corneal surface can be fit as described herein, for example with polynomials as described herein. The fit corneal surface can be used to determine the corneal topography and treatment parameters as described herein. The corneal profile data may comprise coordinate system 600A, for example.

FIG. 6B shows a distorted coordinate system 600B overlaid on the eye image 601B of the eye 43. The image 601A of the eye 43 shows various anatomical features including the sclera 43SC, the limbus 43LI, the iris 43I, and the pupil 43PU. In many embodiments, this image 601B is taken of the eye by a visual imaging system of the laser eye surgery system 2. This image 601B is taken when the anterior surface of the eye 43 is coupled with a suction ring of the laser eye surgery system 2 to expose the anterior surface to air. The suction ring may distort the tissue structures of the eye 43 when placed thereon. The locations of the various tissue structures of the eye, such as one or more structures of the iris, in relation to the distorted coordinate system 600B can be mapped to their respective locations the coordinate system 600A in image 601A to account for this distortion.

FIG. 6C shows a distorted coordinate system 600C overlaid on the eye image 601C of the eye 43. The image 601C of the eye 43 shows various anatomical features including the sclera 43SC, the limbus 43LI, the iris 43I, and the pupil 43PU. In many embodiments, this image 601C is taken of the eye by a visual imaging system of the laser eye surgery system 2. This image 601C is taken when the anterior surface of the eye 43 is coupled with a suction ring of the laser eye surgery system 2 and the suction ring is filled with a liquid such as saline or viscoelastic substance. In addition to distortion from interfacing with the suction ring, the refractive properties of the liquid may also distort light reflecting back from the anterior surface of the eye EY. The locations of the various tissue structures of the eye, such as one or more structures of the iris, in relation to the distorted coordinate system 600C can be mapped to their respective locations the coordinate system 600A in image 601A to account for these distortions. Alternatively or in combination, the structures can be mapped to eye coordinate reference system 150

FIG. 6C1 shows corneal profile data 610C of cornea CO for the coordinate system and image of FIG. 6C. The corneal profile data 610C can be provided with mapping of the corneal profile data 610A, or based on a second set of similar measurements. The corneal profile data 610C comprises a plurality of corneal profiles from the tomography system taken with the patient interface away from the eye as in FIG. 6A. The plurality of corneal profiles comprises a first corneal profile 612C, a second corneal profile 614C and a third corneal profile 616C. Additional corneal profiles can be taken. The cornea profiles can be obtained with tomography scans along a plane for example, and detection of the corneal surface. The corneal surface can be fit as described herein, for example with polynomials as described herein. The corneal profile data 610C may a coordinate system 600C overlaid. The corneal profile data 610C of coordinate system 600C may be mapped to eye coordinate reference 150 as described herein, for example. Alternatively or in combination, the corneal profile data 610C may comprise eye coordinate reference 150 as described herein, for example when the treatment is mapped based on the patient interface coupled to the eye.

In many embodiments, the non-distorted image 601A is modified to provide a distorted first image with a distortion similar to that in images 601B or 601C. The distorted image 601A may then be displayed on the display 56A or other display of the laser eye surgery system 2 or 2A. A user of the laser eye surgery system 2 or 2A can adjust one or more of a location or an angle of the distorted image 601A on the display 56A or other display. Locations of a plurality of laser beam pulses from the cutting laser subsystem 44 can then be adjusted in response to the location or the angle of the first distorted image 601A on the display 56A or other display. In some embodiments, the distorted first image 601A is overlaid on the distorted image 601B or 601C on the display 56A or other display to determine the position and the angle of the eye for treatment. A processor of the laser eye surgery system 2 or 2A can determine the position and the angle of the distorted first image 601A on the display in response to user input to adjust the locations of the plurality of laser beam pulses from the cutting laser subsystem 44.

FIG. 6A2 shows corneal thickness profile data for the coordinate system and images of FIGS. 6A and 6A1. The corneal profile data 610A comprises a plurality of corneal thickness profiles from the tomography system taken with the patient interface away from the eye as in FIG. 6A. The plurality of corneal profiles comprises a first corneal thickness profile 617A, a second corneal thickness profile 618A and a third corneal profile 619A. Additional corneal profiles can be taken.

Each of the thickness profiles may comprise a difference between an anterior surface profile and a posterior surface profile, for example. The first corneal thickness profile 617A may comprise a difference between a first anterior surface profile 612A and a first posterior surface profile 611A. The second corneal thickness profile 618A may comprise a difference between second anterior surface profile 614A and a second posterior surface profile 613A. A third corneal profile 619A may comprise a difference between third anterior surface profile 616A and a third posterior surface profile 615A. Additional corneal profiles can be taken.

Each of the corneal thickness profiles coordinate system 600AC of can be mapped to the physical eye coordinate reference system 150.

FIG. 6C2 shows corneal thickness profile data for the coordinate system and images of FIGS. 6C and 6C1. The corneal thickness profile data 610A comprises a plurality of corneal thickness profiles from the tomography system taken with the patient interface away from the eye as in FIG. 6C. The plurality of corneal profiles comprises a first corneal thickness profile 617C, a second corneal thickness profile 618C and a third corneal profile 619C. Additional corneal profiles can be taken.

Each of the thickness profiles may comprise a difference between an anterior surface profile and a posterior surface profile, for example. The first corneal thickness profile 617C may comprise a difference between a first anterior surface profile 612C and a first posterior surface profile 611C. The second corneal thickness profile 618C may comprise a difference between second anterior surface profile 614C and a second posterior surface profile 613C. A third corneal profile 619C may comprise a difference between third anterior surface profile 616C and a third posterior surface profile 615C. Additional corneal profiles can be taken.

Each of the corneal thickness profiles coordinate system 600C of can be mapped to the physical eye coordinate reference system 150.

FIG. 6A3 shows a corneal thickness profile map 620A for the coordinate system and images of FIG. 6A, 6A1 and 6A2. The thickness profile map generally comprises a representation of three dimensional thickness profile data of the cornea, and may comprise three dimensional thickness data of the cornea. For example, the thickness profile data may comprise a two dimensional array in which the thickness of the cornea is stored for each two dimensional location of the array.

The corneal thickness profile map 620 can be determined based on the first corneal thickness profile 617A, the second corneal thickness profile 618A and the third corneal thickness profile 619A, for example. The corneal thickness profile map 620A can be shown in relation to the pupil 43PU and the limbus 43LI. The cornel thickness profile map 620A can be displayed to the user in one or more of many known formats such as with color coding of thicknesses or with equal depth contour lines. The equal depth contour lines may comprise a first equal depth contour line 622A, a second equal depth contour line 624A. The corneal thickness profile data can be fit as described herein, for example with a polynomial as described herein, in order to provide the corneal thickness profile map 620. The maps can be obtained with reference to coordinate system 600A and mapped to eye coordinate reference system 150, for example.

FIG. 6C3 shows a corneal thickness profile map 620C for the coordinate system and images of FIG. 6C, 6C1 and 6C2. The corneal thickness profile map 620C can be determined based on the first corneal thickness profile 617C, the second corneal thickness profile 618C and the third corneal thickness profile 619C, for example. The corneal thickness profile map 620C can be shown in relation to the pupil 43PU and the limbus 43LI. The cornel thickness profile map 620C can be displayed to the user in one or more of many known formats such as with color coding of thicknesses or with equal depth contour lines. The equal depth contour lines may comprise a first equal depth contour line 622C, a second equal depth contour line 624C. The corneal thickness profile data can be fit as described herein, for example with a polynomial as described herein, in order to provide the corneal thickness profile map 620. The maps can be obtained with reference to coordinate system 600C and mapped to eye coordinate reference system 150, for example.

Work in relation to embodiments of the present disclosure suggest that the corneal thickness profile maps and data as disclosed herein are resistant to mechanical deformation when the suction ring is placed on the eye, and can be used to align the eye about the cyclotorsion al axis, for example. The corneal thickness profile maps can be particularly well suited to align eyes having prior refractive surgery, such as eyes that have received LASIK or PRK or other refractive surgery, for example.

The laser surgery system according to the present invention preferably includes an axis determining subsystem. The axis determination subsystem general refers to those portion of the laser surgery system 2 which operate cooperatively to identify and measure axis information regarding one or more ophthalmic axes of the eye. The axis information preferably comprises the location of the selected axis. The one or more selected ophthalmic axes may be of one or more of an optical axis, a treatment axis a visual axis and a fiducial marker axis.

Figure 7A:
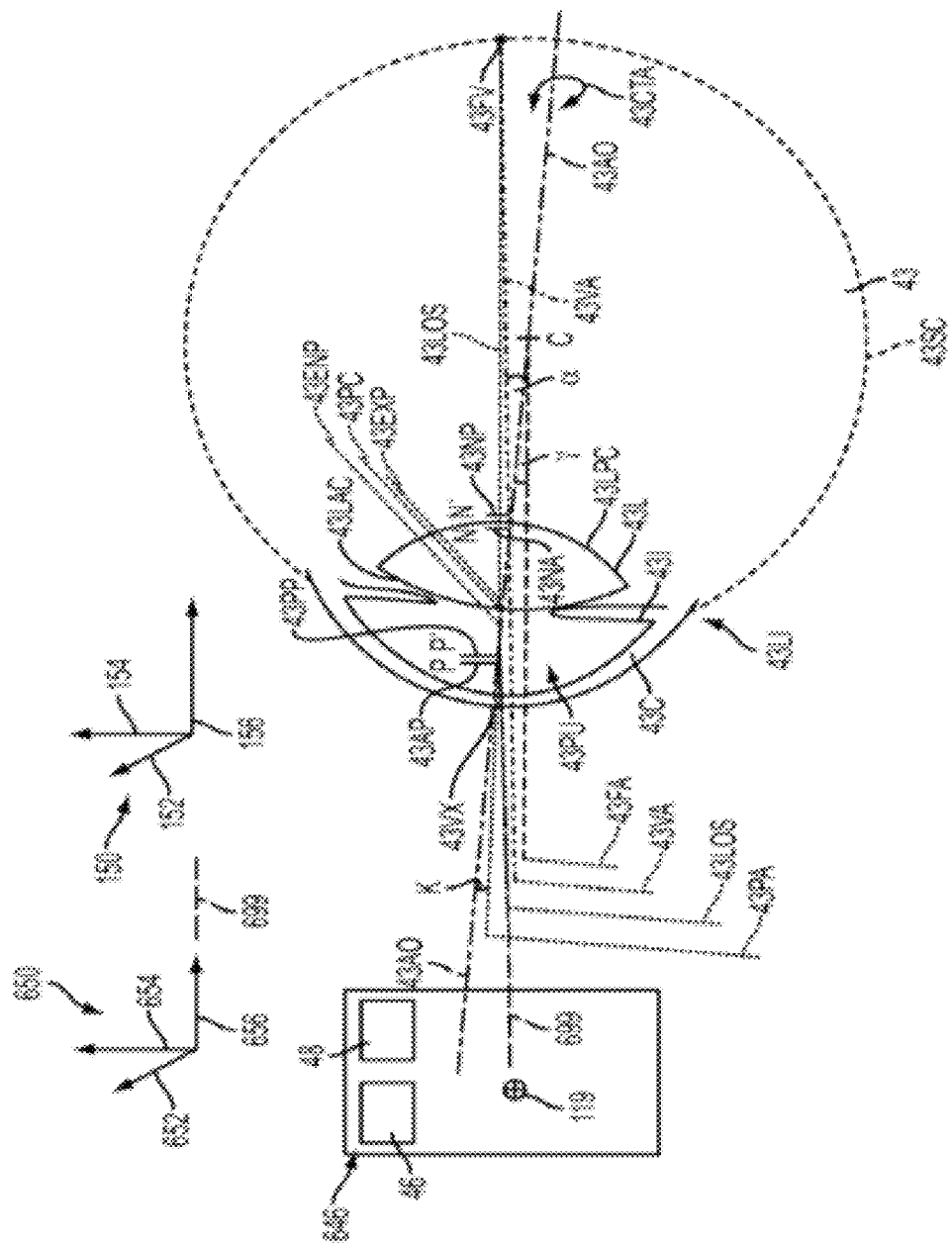
FIGS. 7A and 7B show side views of axes of the eye when the eye views a fixation target and the eye is measured prior to contacting a patient interface, in accordance with many embodiments.
Figure 7B:
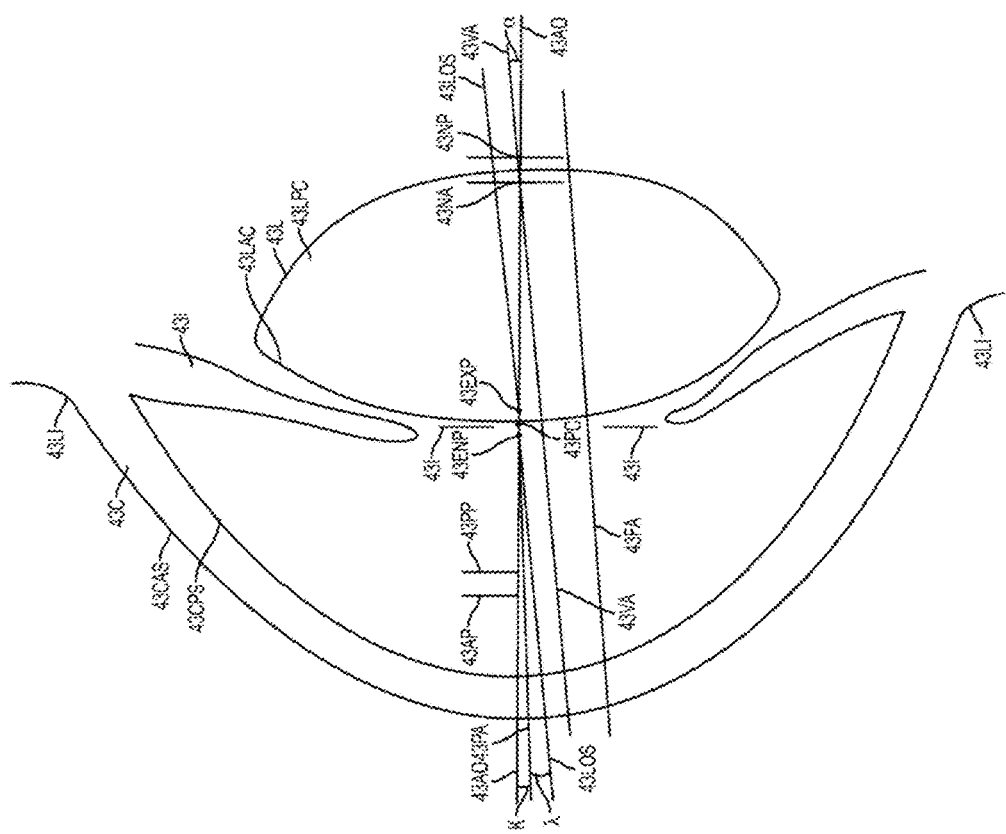

FIGS. 7A and 7B show side views of a plurality of axes of the eye 43 when the eye views a fixation target and the eye is measured with an imaging system 646 prior to contacting a patient interface. The imaging system 646 can be used to measure one or more optical structures of the eye, and the processor of the laser system can be used to determine locations of the incisions in response to locations of the one or more optical structures. The imaging system 646 may comprise one or more components of the ranging system 46 as described herein alignment and may comprise one or more components of guidance system 48 as described herein, for example the OCT system of ranging system 46 and video camera of alignment guidance system 48. Alternatively or in combination, the imaging system 646 may comprise one or more components of separate diagnostic system 648 as described herein. The imaging system 646 may by located on laser system 2, or may comprise separate and distinct ancillary diagnostic system 648, and combinations thereof, for example.

Imaging system 646 can be aligned with one or more axes of the eye as described herein, for example with the patient viewing the fixation light 119. In many embodiments, the patient views fixation light 119, and the imaging system 646 is aligned with the eye in one or more of many ways as described herein.

Imaging system 648 comprises fixation light 119 as described herein for the patient to view when measurements are obtained. The fixation light 119 allows the patient to fixate in order to align the axes of the coordinate system 150 of the eye with one or more reference axes of the coordinate system 650 of imaging system 646. The imaging system may 648 comprise a measurement axis 699 that extends along an optical axis of the measurement system, and the fixation light 119 can be located along the measurement axis 699 to align the eye with the measurement system. The measurement axis 699 may comprise axis 99 of the optical delivery system of laser system 2 when laser system 2 is used for measurements of the eye prior to contacting the eye with the patient interface. The initial measurement reference coordinate system 650 of imaging system 646 comprises a first dimension 652, a second dimension 654 and a third dimension 646, for example. The dimensions of the coordinate system 650 may comprise a right handed triple orthogonal coordinate reference system, for example. The third dimension 646 may comprise the measurement axis 699 of the measurement system, for example. For initial measurements of the eye prior to the patient interface contacting the eye, the coordinate reference system may comprise the eye coordinate reference system 150 as described herein. When the eye has been contacted with the patient interface, the eye coordinate reference system 150 for treatment with the laser can be one or more of rotate or translated with respect to the initial measurement reference coordinate system 650.

The imaging system 646 includes sensors to image one or more tissue structures of the eye and can be used to determine one or more axes of the eye as described herein. The imaging system 646 can image and profile one or more structures of the eye as described herein, such as one or more of the cornea of the eye 43C, the anterior surface of the cornea, the posterior surface of the cornea, the iris of the eye 431, the pupil of the eye 43PU, the natural pupil of the eye 43PUN, the lens of the eye 43L, the anterior capsule of the lens 43LAC, the posterior capsule of the lens 43LPC, the entrance pupil of the eye 43ENP, the natural entrance pupil of the eye, the vertex of the cornea 43VX. In many embodiments, tomography of the cornea is combined with surface topography of the cornea and the video camera images of the cornea to determine one or more axes of the eye 43.

The vertex 43VX of the cornea may comprise a central part of the cornea located along the optical axis 43AO of the eye that extends substantially perpendicular to the plane of the eye, and may comprise a center of the cornea as determined in response to a measurement of the limbus extending around the perimeter of the cornea.

The imaging system 646 can be used to determine one or more optical structures of the eye when the eye fixates naturally without contacting the patient interface in order to determine locations of the one or more optical structures of the eye when the eye contacts the patient interface. In many embodiments, the imaging system 646 is used to determine one or more of the optical axis of the eye 43AO, the center of curvature of the anterior corneal surface, the center of curvature of the posterior corneal surface, the center of curvature of the lens capsule anterior surface, or the center of curvature of lens capsule posterior surface. The optical axis of the eye may comprise a straight line extending from the center of curvature of the anterior surface of the cornea to the center of curvature of the posterior surface of the posterior lens capsule. In many embodiments, the centers of curvature may not lie on a straight line, and the processor of the laser eye surgery system can be used to determine the optical axis 43AO with an orientation and location that decreases the distance from the optical axis to each of the center of curvature of the cornea anterior surface, the center of curvature of the cornea posterior surface, the center of curvature of the lens capsule anterior surface, and center of curvature of the capsule posterior surface, for example, with least squares fitting of the optical axis to the centers of curvature for example.

The curvatures and the centers of curvature of the eye can be used to determine the locations of the cardinal points of the eye comprising the object point where the fixation light 119 is located, the image point where the center of the fovea 43FV is located when the patient views the fixation light, the anterior nodal point 43NA of the eye, the posterior nodal point 43NP, the anterior principal point 43AP, and the posterior principal point 43PP. One or more of these cardinal points of the eye can be used to determine incision locations of the pulsed laser beam, and these cardinal points and the corresponding axes can be shown on a display to a user to determine locations on the incisions, in accordance with many embodiments.

One or more of the natural entrance pupil 43ENP or the natural exit pupil 43EXP of the eye can be determined and may be used to determine locations of the incisions with the pulsed laser beam. The entrance pupil 43ENP of the eye comprises a virtual image of the pupil of the eye as seen by light rays entering the eye from the fixation light 119. The natural exit pupil of the eye 43EXP may comprise the image of the iris 43I formed by lens 43I as seen from the fovea.

Referring to FIG. 7B, the cardinal points of the eye and image forming axes of the eye are shown in detail. The iris 43I can be seen in relation to the physical pupil center 43PC, the location of the center of the entrance pupil 43ENP along the optical axis 43AO, and the location of the center of the exit pupil 43EXP along the optical axis 43AO. The visual axis 43VA is shown extending from the fixation light to the anterior node 43NA, and from the posterior node 43NP to the center of the fovea, with the first and anterior node separated from the second and posterior node along the optical axis 43AO. The line of sight 43LOS can be seen extending from the fixation light 119 to the center of the entrance pupil 43ENP, and from the center of the exit pupil 43EXP to the center of the fovea, with the center of the entrance pupil and the center of the exit pupil located along the optical axis.

The axes of the eye that can be identified and determined with the imaging system 646 or the processor of laser system (and combinations thereof) include a fixation axis 43FA, a visual axis 43VA, a line of sight 43LOS, a pupillary axis 43PA and an optical axis 43AO.

The 43FA fixation axis of the eye may comprise an axis extending from the fixation light 119 through a center of rotation of the eye 43C.

The line of sight 43LOS may comprise a straight line extending from the fixation light through the center of the entrance pupil 43EP when the patient views the fixation light. The line of sight 43LOS may also comprise a straight line extending from the fovea to the exit pupil of the eye when the patient views the fixation light. The entrance pupil P comprises a virtual image of the pupil that the light rays from the fixation light entering the eye are directed toward, and can be imaged with the video camera of the alignment assembly 48 as described herein. The exit pupil 43EXP comprises The pupillary axis 43PA may comprise a line perpendicular to the surface of the cornea, passing through the center of the pupil, for example.

The visual axis of the eye may comprise one or more of many axes of the eye, in accordance with embodiments as described herein. In many embodiments the visual axis comprises an axis extending from the fixation light 119 to the anterior optical nodal point of the eye N, in which the anterior optical nodal point of the eye N is located along the optical axis of the eye 43AO. The visual axis of the eye can extend from the posterior nodal point of the eye 43NP to the center of the fovea FV, with an angle α (Alpha), extending between the optical axis and the visual axis.

Alternatively, the visual axis of the eye may comprise an imaginary straight line passing from the fixation light located at the midpoint of the visual field, through the pupil, to the center of the fovea 43FV when the patient fixates on the fixation light, for example. A person of ordinary skill in the art, based on the teachings of the present disclosure, will recognize that the imaginary straight line of the visual axis can be approximated by a line extending between the anterior nodal point of the eye and the posterior nodal point of the eye, for example approximated with a single "nodal" point of the eye. For example, the eye may comprise a single index of refraction to provide the single nodal point of the eye, for example with Gullstrand's reduced schematic eye model. However, in many embodiments as described herein the eye comprises two or more indices of refraction, for example three or more indices of refraction, and the image guided treatment as described herein will provide treatment planning to the user in response to identification of the visual axis of the eye extending from the anterior nodal point of the eye to the fixation target and from the posterior nodal point of the eye to the fovea.

An angle γ (Gamma) can extend between the optical axis and the fixation axis, for example. An angle κ (Kappa) can extend between the visual axis 43VA and the pupillary axis 43PA, for example. Alternatively, angle κ (Kappa) can be defined so as to extend between the pupillary axis 43PA and the line of sight, for example. In many embodiments, the pupillary axis comprises a line extending normal to the surface of the cornea and through the center of the pupil, for example.

Figure 7C:
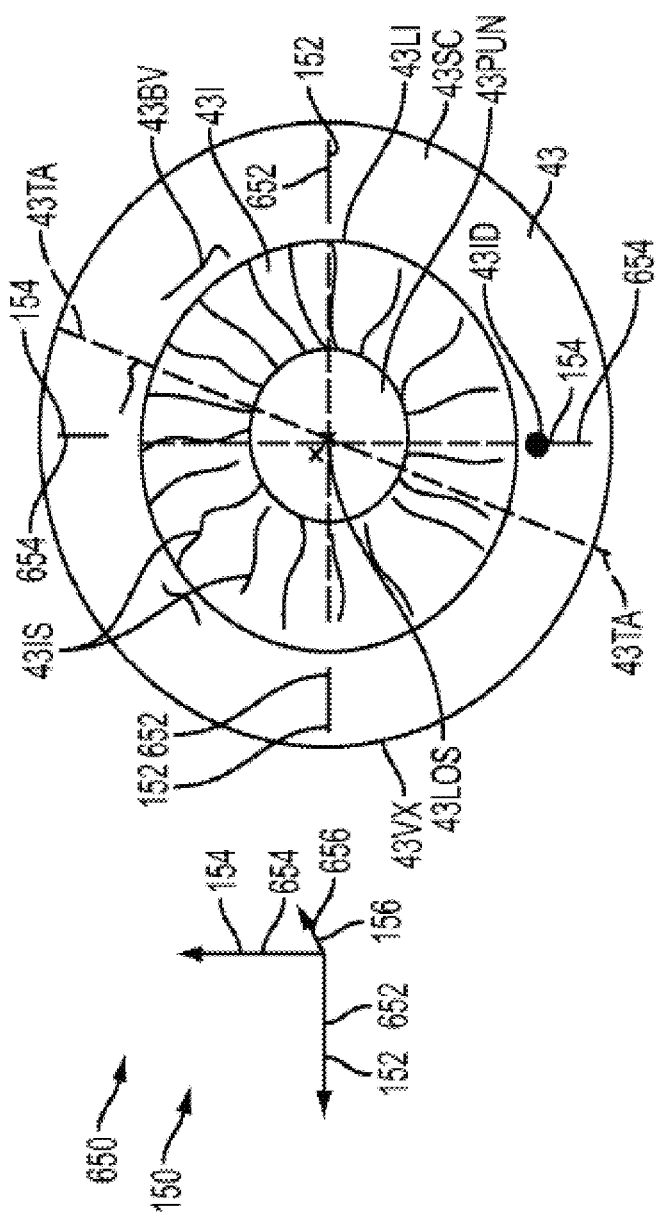
FIG. 7C shows an anterior view of an eye as in FIGS. 7A and 7B, in accordance with embodiments.
Figure 7D:
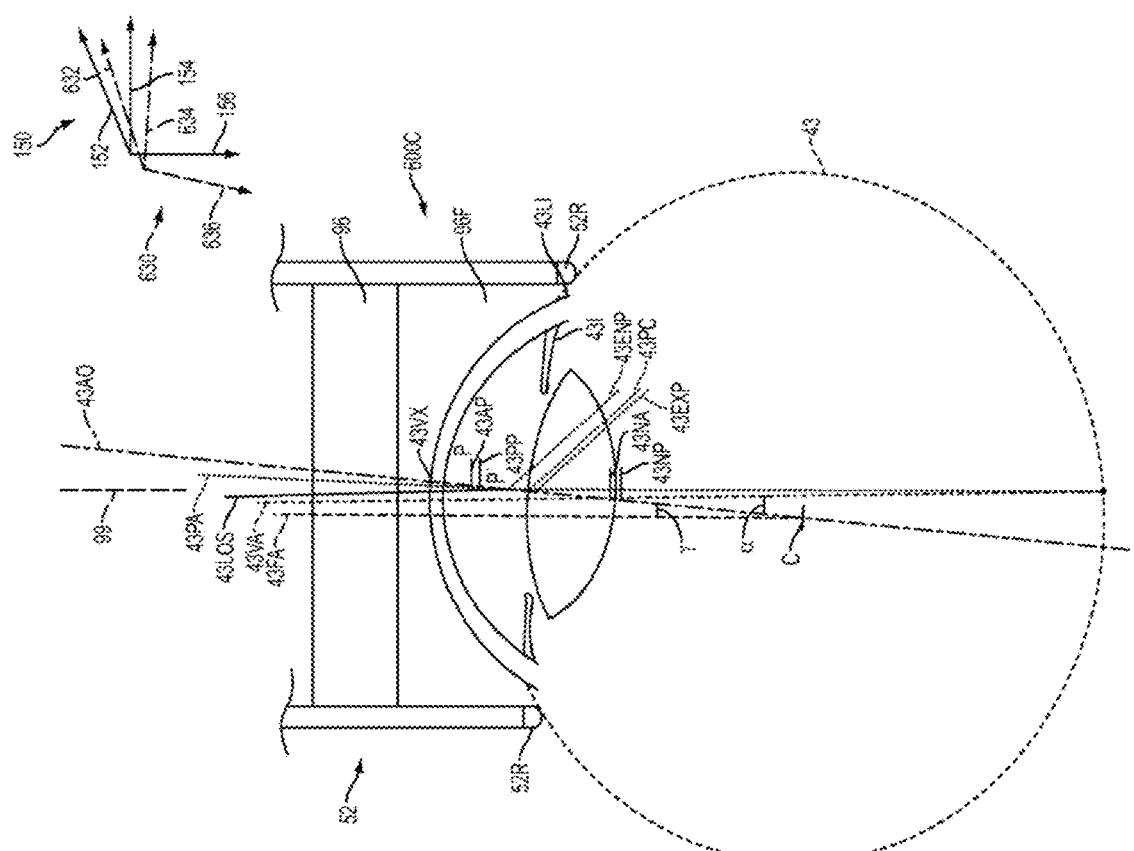
FIGS. 7D and 7E show the eye as in FIGS. 7A to 7C coupled to a patient interface for treatment, in accordance with many embodiments.

FIG. 7C shows an anterior view of an eye 43 as in FIGS. 7A and 7B. The view shows structure of the eye similar to the views of FIGS. 7A and 7B. In many embodiments, the images of FIGS. 7A and 7B are obtained with a tomography system such as an OCT system and the image of FIG. 7C is obtained with a video camera such as an alignment camera as described herein. The dimensions of coordinate system 650 can be aligned for each of the measurement systems of measurement system 150, and can define the measurement axis of the eye.

The image of the eye may comprise one or more structures that can be used to identify one or more treatment axes of the eye and structures and optical tissue surfaces of the eye as described herein, which can be combined with data from one or more of the tomography or the tomography system as described herein to determine treatment axis and alignment of the eye, for example. The structure of the image of the eye may comprise an image of a marker of the eye such as an ink dot 43ID placed by a health care provider such as a physician or an ophthalmic technician, which can be used for alignment of the eye such as cyclo torsional alignment of the eye around one or more optical axes of the eye as described herein. The ink dot 43ID may comprise a plurality of ink dots, for example a plurality of ink dots on a plurality of opposing sides of the pupil. The structure of the image of the eye may comprise images of blood vessels 43BV that can be used for alignment of the eye, such as cyclo torsional alignment of the eye around one or more axes of the eye as described herein, for example. The structure image of the eye may comprise structure of the iris that can be used for alignment of the eye, such as torsional alignment of the eye around one or more axes of the eye as described herein, for example.

The eye may comprise one or more treatment axes, such as treatment axis 43TA, and the location of treatment axis 43TA can depend upon the layer and tissue structure of the eye being treated, for example the lens or the cornea. The treatment axis 43TA may comprise an axis of an aberration of the eye such as an astigmatism of the eye or a higher order aberration of the eye such as coma or trefoil of the eye, for example. The treatment axis 43A can be identified by the system user such as a physician, and can be defined to have a center corresponding to one or more of the optical axes as described herein such as one or more of the vertex of the cornea, the line of sight of the eye, the visual axis of the eye, or the visual axis of the eye extending from the anterior node of the eye. Alternatively or in combination, the axis identified by the user can be different for the type of treatment of the eye. For example, with arcuate incisions such as limbal relaxing incisions, the treatment axis may comprise the line of sight or the vertex of the cornea, or other axis as described herein. With an intraocular lens to be placed, the treatment axis may comprise a center of the real pupil, a center of the line of sight, a center of the visual axis extending from an anterior node of the eye, or other axis as described herein, for example. Merely by way of example in accordance with embodiments, the treatment axis 43A is shown with reference to the line of sight 43LOS corresponding to the center of the entrance pupil when the patient fixates on light 119 and the eye is viewed with the video camera as described herein, for example.

The eye may comprise one or more fiducial marker axes or meridians 43FMA, and the location of fiducial marker axis or meridian 43FM can depend upon the layer and tissue structure of the eye being treated, for example the lens or the cornea. The fiducial marker axis 43FMA is preferably an axis or meridian of an aberration of the eye such as an astigmatism of the eye or a higher order aberration of the eye such as coma or trefoil of the eye, for example, and may be the same or different from the treatment axis 43TA. The fiducial marker axis 43FMA can be identified by the system user such as a physician, and can be defined to have a center corresponding to one or more of the optical axes as described herein such as one or more of the vertex of the cornea, the line of sight of the eye, the visual axis of the eye, or the visual axis of the eye extending from the anterior node of the eye. With an intraocular lens to be placed, the fiducial marker axis may comprise a center of the real pupil, a center of the line of sight, a center of the visual axis extending from an anterior node of the eye, or other axis as described herein, for example.

Figure 7F:
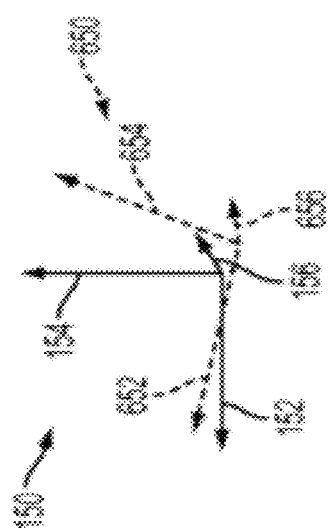
FIG. 7F shows coordinate transformations of the measurement coordinate reference system prior to contacting the eye with the laser system and the measurement coordinate reference system when the eye contacts the patient interface as in FIGS. 7D and 7E.
Figure 7E:
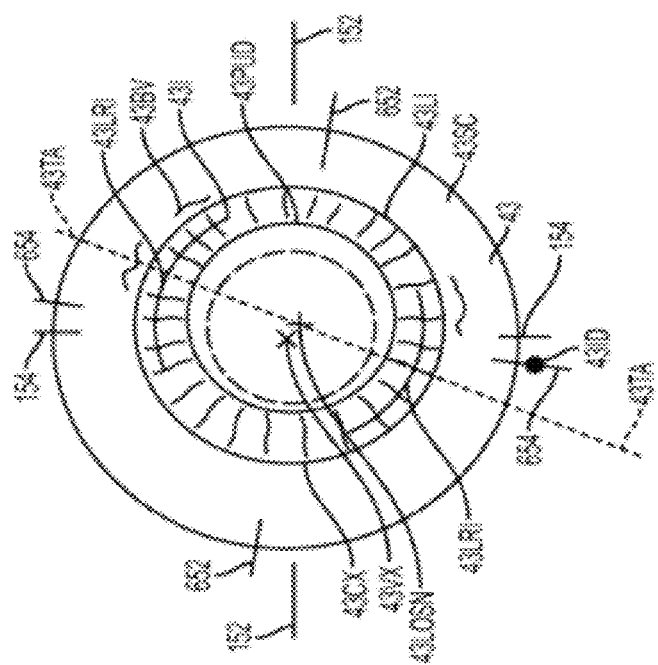

FIG. 7F shows rotation and translation of the measurement coordinate reference system 650 relative to the eye coordinate reference system 150 when the eye has contacted the patient interface, in which the rotation and translation of the measurement system 650 prior to contact with the patient interface corresponds to rotation and translation of the eye relative to the coordinate system 150 when the patient interface contacts the eye. The rotation and translation of one or more of the tissue structures of the eye determined with the natural pupil and vision of the eye can be correspondingly rotated and translated and provided on a display for the physician to determine the treatment of the eye. The locations and orientations of the tissue structures of the eye determined with measurements of the eye prior to coupling with the patient interface can be mapped from the coordinate system 650 to the coordinate 150 and shown on the display with the image of the eye coupled to patient interface. This allows the user to determine the treatment with the coordinate reference 150 with the eye contacting the patient interface, while showing the locations of the structures of the eye from used for natural vision from the coordinate reference frame 650 on the patient interface.

Figure 7G:
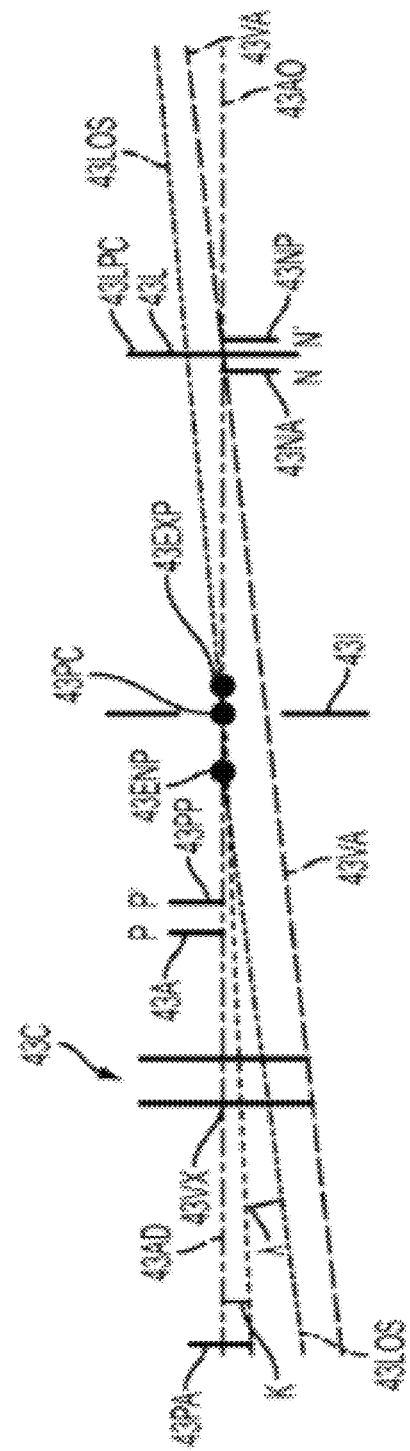
FIG. 7G shows an optical schematic of the eye as in FIGS. 7A and 7B.

FIG. 7G shows an optical schematic of the eye as in FIGS. 7A and 7B, with structures of eye including the cardinal points of the eye and axes of the eye useful for vision. In many embodiments, one or more structures of the optical schematic of the eye are projected onto the display and aligned with the image of the eye shown on the display in order for the user to plan the incisions and surgical treatment of the eye.

In many embodiments, one or more of the tissue structures of each of images 7A to 7G can be shown on the display to the user for planning the locations of incisions as described herein, such as the location of the nodal points of the eye along the optical axis of the eye, the line of sight of the eye, the vertex of the cornea, and the visual axis extending from the anterior nodal point of the eye. For example, the one or more structures of the optical schematic of the eye determined from measurements prior to contacting the eye can be shown on the display aligned with images of the eye obtained when the patient interface has contacted the eye, in order for the surgeon to determine the locations of incisions in alignment with the one or more structures of the eye determined from measurements obtained prior to contact with the patient interface when the patient interface contacts the eye. Alternatively or in combination, the one or more optical structures of the eye shown on the display can be determined in response to measurements obtained when the patient interface contacts the eye, for example for comparison with locations of the one or optical structures determined from measurements obtained prior to the patient interface contacting the eye.

The average axial length of the adult human eye is about 24 mm. Since the full range imaging depth of the OCT measurements are only about 5 mm to 8 mm, then OCT scanning of the invention may provide for OCT scans at different depths of the eye that can be combined together to determine various biometry measurements, including the axial length, to determine corneal shape information and to determine lens shape information. The OCT measurements of the present invention preferably includes OCT imaging at various depths of the patient's eye for imaging 1) at least a portion of the retina, 2) at least a portion of the anterior portion of the eye, including at least a portion of the cornea (anterior and posterior), iris, and lens (anterior and posterior), and 3) performing axial eye length measurements.

In many embodiments, the controller is coupled to an Optical Coherence Tomography (OCT) subsystem of the ranging subsystem. The OCT subsystem is preferably configured to sequentially scan the eye in a plurality of OCT scan patterns, each scan pattern being at a different axial depth of a patient's eye as shown graphically in FIG. 9A. The plurality of scan patterns comprise an anterior segment OCT scan pattern in a region at or near a location of a cornea, preferably a region including the anterior surface of the cornea and the posterior surface of the cornea, shown as region "A" in FIG. 9A. The plurality of scans may be in an axial or lateral directions. Scans in region "A" may for instance be selected to provide corneal surface information regarding the axial position of the anterior surface of the cornea, the shape of the anterior surface of the cornea, the axial position of the posterior surface of the cornea, and the shape of the posterior surface of the cornea. The plurality of scan patterns preferably also comprise a lenticular OCT scan pattern at or near a location of a lens, preferably in a region including the anterior surface of the lens and the posterior portion of the lens, shown as region "B" in FIG. 9A. The plurality of scans may be in an axial or lateral directions. Scans in region "B" may for instance be selected to provide lens surface information regarding the axial position of the anterior surface of the lens, the shape of the anterior surface of the lens, the axial position of the posterior surface of the lens and the shape of the posterior surface of the lens, and the equator of the lens. The plurality of OCT scan patters further preferably comprises a retinal OCT scan pattern at or near a location of a retina, which may include a portion of the posterior pole of the axially anterior to the retina, as shown in region "C" in FIG. 9A. The plurality of imaging scan patterns preferably comprises an OCT scan pattern suitable to measure a plurality of an anterior corneal surface, a corneal pachymetry, a central corneal thickness, and an anterior chamber depth of a patient's eye. The plurality of imaging scan patterns preferably also comprises a lenticular OCT scan segment scan pattern suitable to measure a plurality of a lens thickness, an anterior lens surface, and a posterior lens surface. The plurality of imaging scan patterns comprises a retinal OCT segment scan pattern suitable to measure at least the axial length.

Figure 9A:
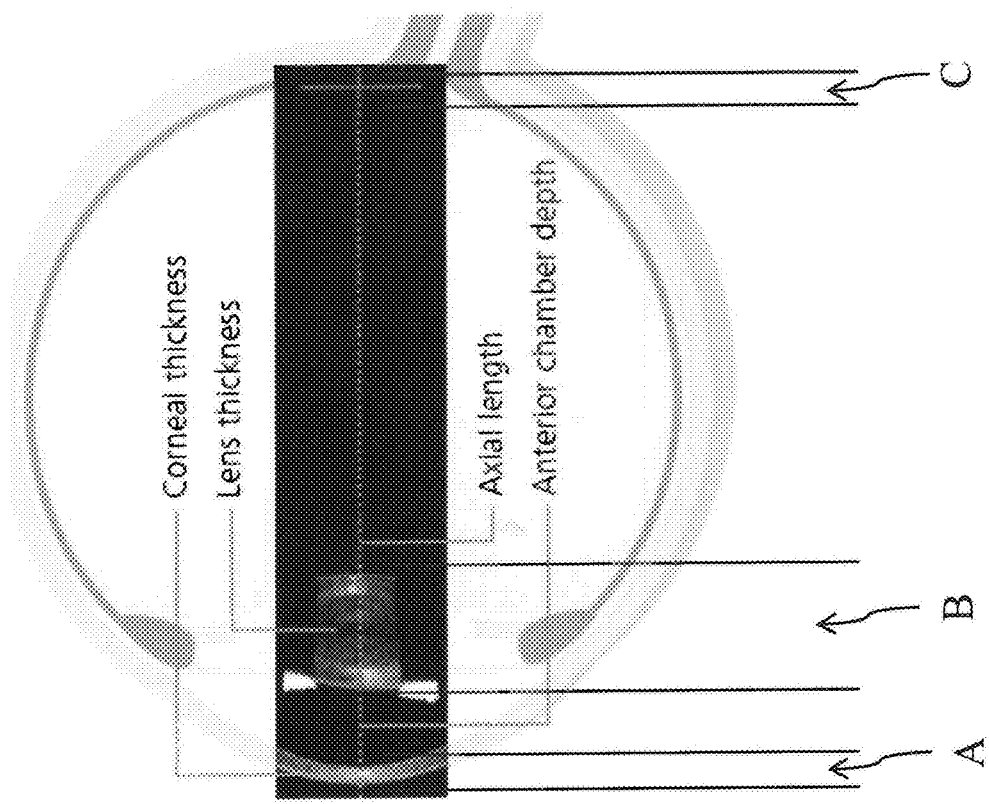
FIG. 9A shows scanning regions in the eye of an optical coherence tomography apparatus according to many aspects of the present invention and FIG. 9B shows a flow chart of a method of obtaining OCT information at various optical lengths of the eye as shown according to many embodiments.

In many embodiments, the laser surgery system comprises a memory operable to store data acquired from each of the corneal topography subsystem and the Optical Coherence Tomography subsystem, wherein the stored data includes a plurality of ocular biometry information, anterior corneal surface information, posterior corneal surface information, anterior lens surface information, and posterior lens surface information, and lens position information. The ocular biometry information preferably comprises a plurality of a central corneal thickness (CCT), an anterior chamber depth (ACD), a lens thickness (LT), and an axial length (AXL) as shown in FIG. 9A. In many embodiments, the ocular biometry information preferably includes the lens thickness.

In many embodiments, a model of the eye is constructed based on all or some of the stored data, including the data of each of the corneal topography subsystem and the Optical Coherence Tomography subsystem. The data used to construct the model preferably includes a plurality of ocular biometry information, anterior corneal surface information, posterior corneal surface information, anterior lens surface information, and posterior lens surface information, and lens position information. The ocular biometry information used to construct the model preferably comprises a plurality of a central corneal thickness (CCT), an anterior chamber depth (ACD), a lens thickness (LT), and an axial length (AXL) as shown in FIG. 9A. The model of the eye may be performed with the human lens intact in the subject eye. The data, including the ocular biometry information, may be modified based on a measured index of refraction of one or more ocular tissues as discussed herein. In many embodiments, the model is performed using ray tracing.

Figure 9B:
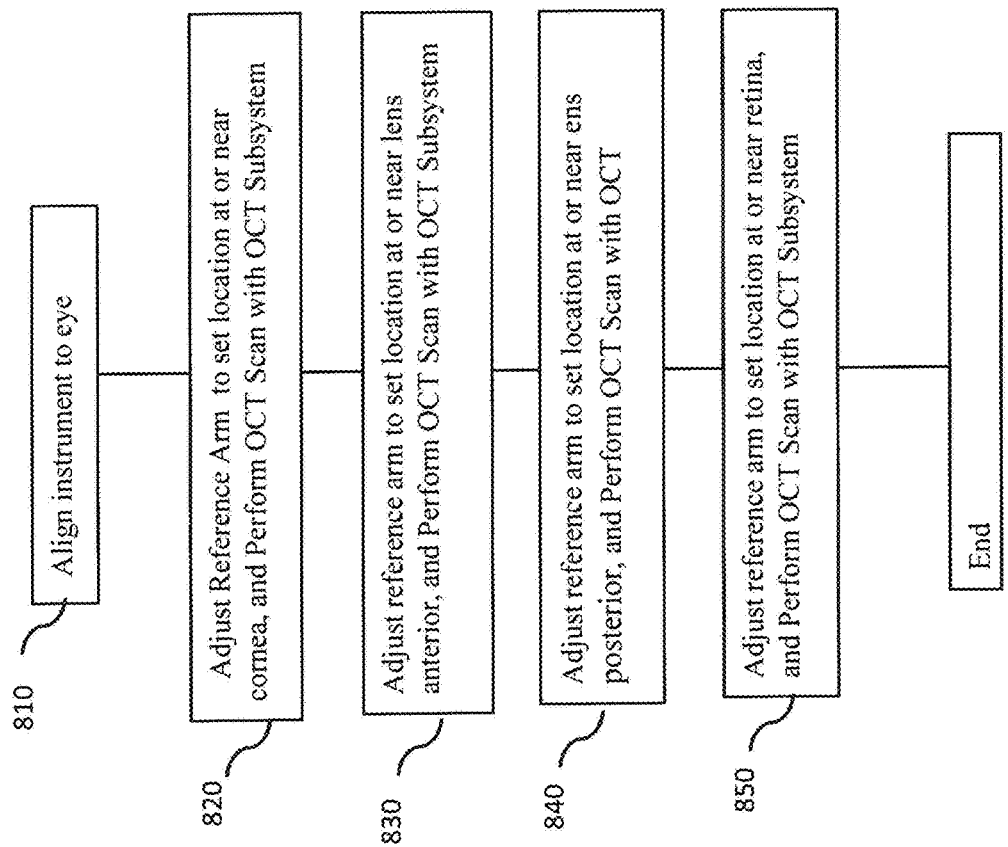

A method of obtaining OCT information at various optical lengths of the eye is shown, for instance, in FIG. 9B. A step 810 comprises aligning the eye with the OCT subsystem. A step 820 comprises adjusting the reference arm to set OCT scan location at or near cornea, and performing an OCT Scan with the OCT Subsystem. A step 830 comprises adjusting the reference arm to set the OCT location at a location at or near the lens anterior and performing an OCT Scan with the OCT Subsystem. An optional step 840 comprises adjusting the reference arm to set the OCT location at a location at or near the lens posterior and performing an OCT Scan with the OCT Subsystem. A step 850 comprises adjusting the reference arm to set the OCT location at a location at or near the retina and performing an OCT Scan with the OCT Subsystem.

The laser surgery system according to the present invention preferably includes a refractive index correcting subsystem. The refractive index correcting subsystem general refers to that portion of the laser surgery system 2 which operate cooperatively to identify and measure the index of refraction of one or more of the ophthalmic tissues. The selected tissues may be one or more selected for the group consisting of the cornea, the aqueous humor, the lens and the vitreous humor. The measured indexes of refraction for the selected tissue can be used to more accurately determine biometry and surface information and thus improve the modeling of the patient's eye, by for example, ray tracing.

In many embodiments, a physical distance can be obtained by dividing the optical path length by the index of refraction of the material through which the light beam passes. Prior to measurement of an actual index of refraction for a selected tissue, a group refractive index may be used and can take into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 mm. The group refractive index of 1.339 differs on the order of 1% for the OCT beam wavelength and spectral bandwidth. Many embodiments herein provide methods for determining the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 10B:
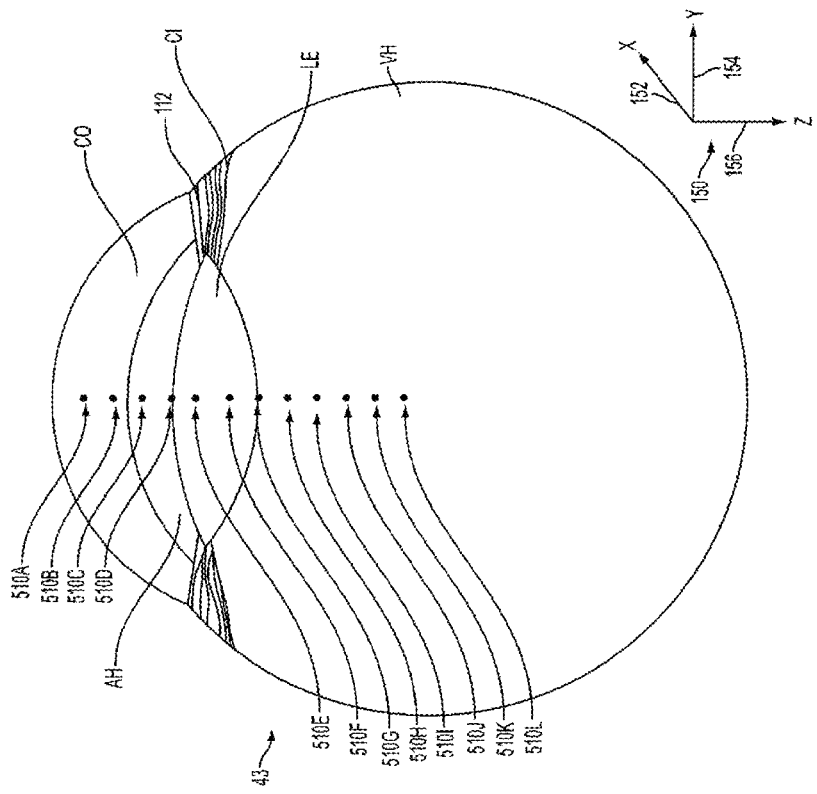
FIGS. 10B and 10C show focal points through various anatomical structures for determining indices of refraction of the various anatomical structures.
Figure 10A:
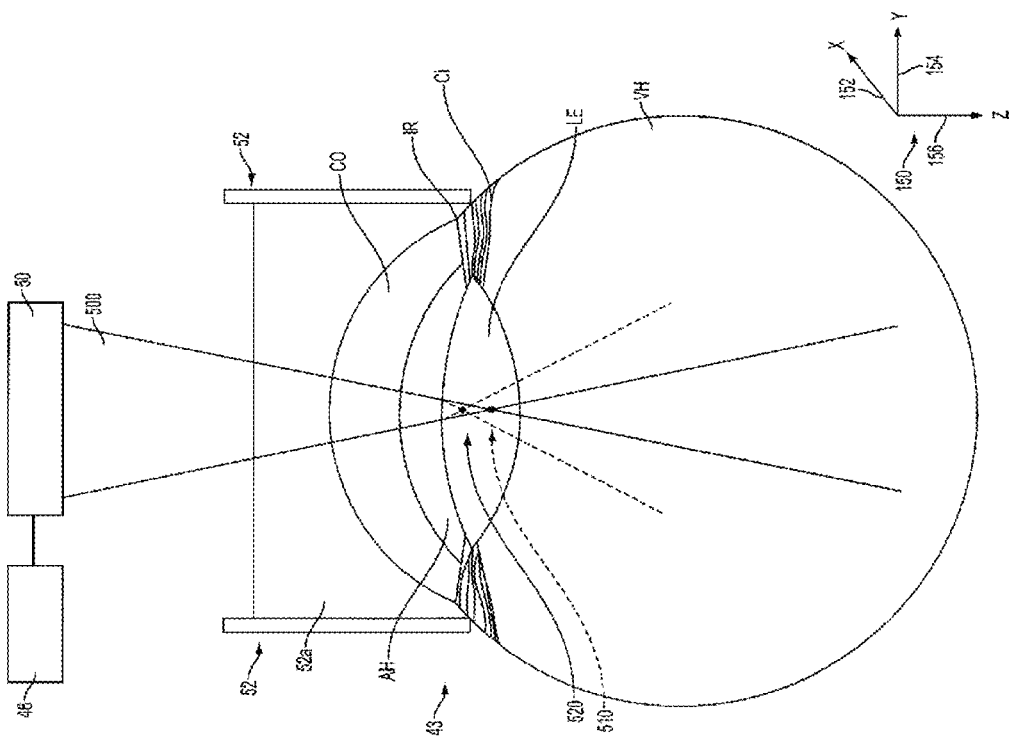
FIG. 10A shows a light source focused onto the lens of the eye to determine an index of refraction of the eye.
Figure 10C:
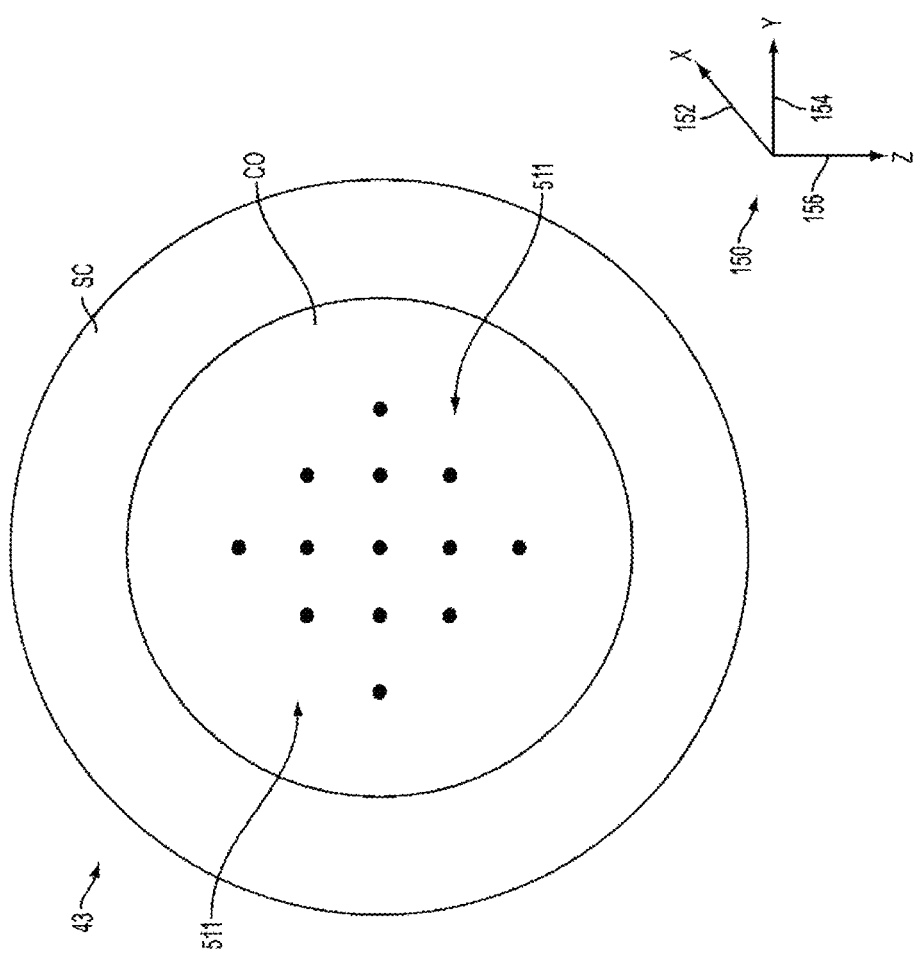

FIG. 10A shows light from shared optics 50 as directed by ranging subsystem 46 focused onto the lens LE of the eye 43. The beam 500 from shared optics 50 can be focused onto a target focal point 510 within the lens LE. The beam 500, however, may instead be focused onto a different target focal point within other anatomical locations in the eye 43 such as a tear film, a cornea CO, an aqueous humor AH, an anterior lens capsule, a lens cortex, an anterior portion of the lens cortex, a posterior portion of the lens cortex, a lens nucleus, a posterior lens capsule, or a vitreous humor VH. FIG. 10A also shows the iris IR and the ciliary muscles CI of the eye 43.

According to many embodiments, the ranging subsystem 46 of the system 2 can be used to determine the indices of refraction of the tissues of the eye 43. As shown in FIG. 10A, the eye 43 is coupled with the patient interface 52 which comprises a suitable liquid 52 a (e.g., a sterile buffered saline solution (BSS) such as Alcon BSS (Alcon Part Number 351-55005-1) or equivalent) is disposed between and in contact with the patient interface lens posterior surface and the patient's cornea CO and forms part of a transmission path between the shared optics 50 and the patient's eye 43.

In many embodiments, the ranging subsystem 46 determines the location of the target focal point 510 in response to predetermined indices of refraction of the anatomical structures of the eye. One or more of the ranging subsystem 46 or the shared optics 50 may accounts for the indices of refraction of the structures between the shared optics 50 and the target focal point 510 to determine the configuration of the shared optics 50 to properly locate and focus the beam 500 onto the target focal point 510. For example, one or more of the XY-scan and Z-scan mechanisms of the shared optics 50 may be adjusted in response to the indices of refraction of the structures between the shared optics 60 and the target focal point 510. As shown in FIG. 10A, to focus the beam 500 onto the focal point 510 within the lens LE, the anatomical structures and materials that need to be taken into account include the suitable liquid 52 a, the cornea CO, the aqueous humor AH, and the lens LE. The index of refraction of the suitable liquid 52 a may be known or can be predetermined. The indices of refraction of the cornea CO and the aqueous humor AH typically do not vary significantly across individuals. The indices of refraction of the lens LE, however, can vary significantly across individuals. Further, the indices of refraction may vary even within the lens LE. The ranging subsystem 46 may first assume an index of refraction for the lens LE, for example, in response to an average lens index of refraction for a patient population. As shown in FIG. 10A, the target focal point 510 may actually be different than the actual focal point 520. Thus, the indices of refraction through the lens LE can be determined and the ranging subsystem 46 may further be configured to take into account the determined indices of refraction. As described herein, the positional differences between the target focal point 510 and the actual focal point 520 can be used to determine the index of refraction of at least a portion of the lens LE.

FIG. 10B show various target focal points 510A, 510B, 510C, 510D, 510E, 510F, 510G, 510H, 510I, 510J, 510K, and 510L through the anatomical structures of the eye EY for determining the indices of refraction of the various anatomical structures. As described here, one or more of the ranging subsystem 46 and the shared optics 50 may be used to determine the positional differences between each of these target focal points and their corresponding actual focal points to determine the index of refraction for the corresponding tissue structure of the eye. As shown in FIG. 5B, the target focal points 510A and 510B may be within the cornea CO; the target focal points 510C and 510D may be within or at the edge of the aqueous humor AH, the target focal points 510E, 510F, and 510G may be within or at the edge of the lens LE, and the target focal points 510H, 510I, 510J, 510K, and 510L may be within the vitreous humor VH.

FIG. 10B shows the target focal points being varied along the vertical or Z-axis 156, for example by adjusting the shared optics 50. As shown in FIG. 5C, target focal points 511 may also be varied along the horizontal axes such as X-axis 152 and Y-axis 154. For example, by varying target focal points up to three dimensionally, i.e., across one or more of the X-axis 152, Y-axis 154, or Z-axis 156, up to a three-dimensional gradient index of refraction profile of an anatomical structure of the eye EY such as the lens LE may be generated. The laser eye surgery system 2 described herein may apply the refractive index profile of the lens LE to more accurately place target focal points within the anatomical structures of the eye which can lead to more precise laser incisions.

Figure 10D:
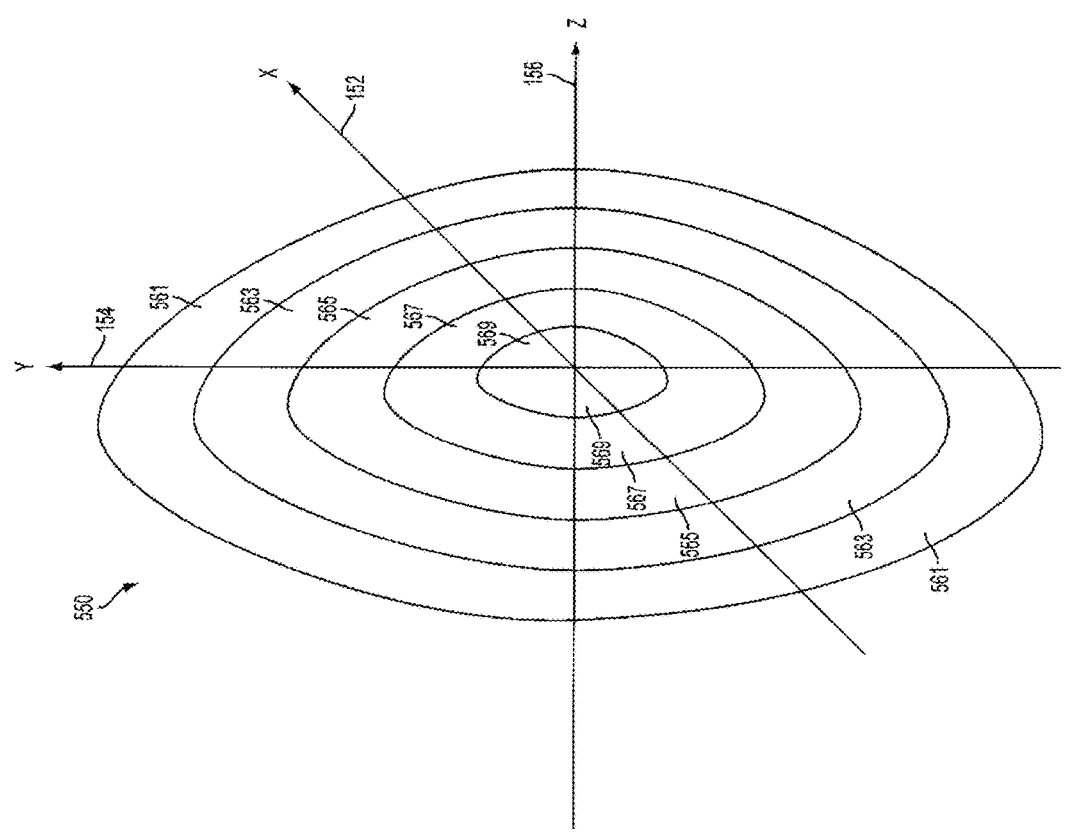
FIG. 10D shows a refractive index profile of a lens of an eye according to many embodiments.

FIG. 10D shows an exemplary refractive index profile 550 of the eye 43. FIG. 10D shows the profile 550 as two-dimensional, i.e., comprises refractive index information of the lens LE in response to position in the Y-axis 154 and the Z-axis 156. The profile 550 may in many embodiments be three-dimensional and comprise refractive index information of the lens LE further in response to position in the X-axis 152. In at least some cases, the indices of refraction in the lens LE may vary within the lens LE. As shown in FIG. 10D, the indices of refraction in the first lens region 561, the second lens region 563, the third lens region 565, the fourth lens region 567, and the fifth lens region 569 may be different from one another.

Figure 11:
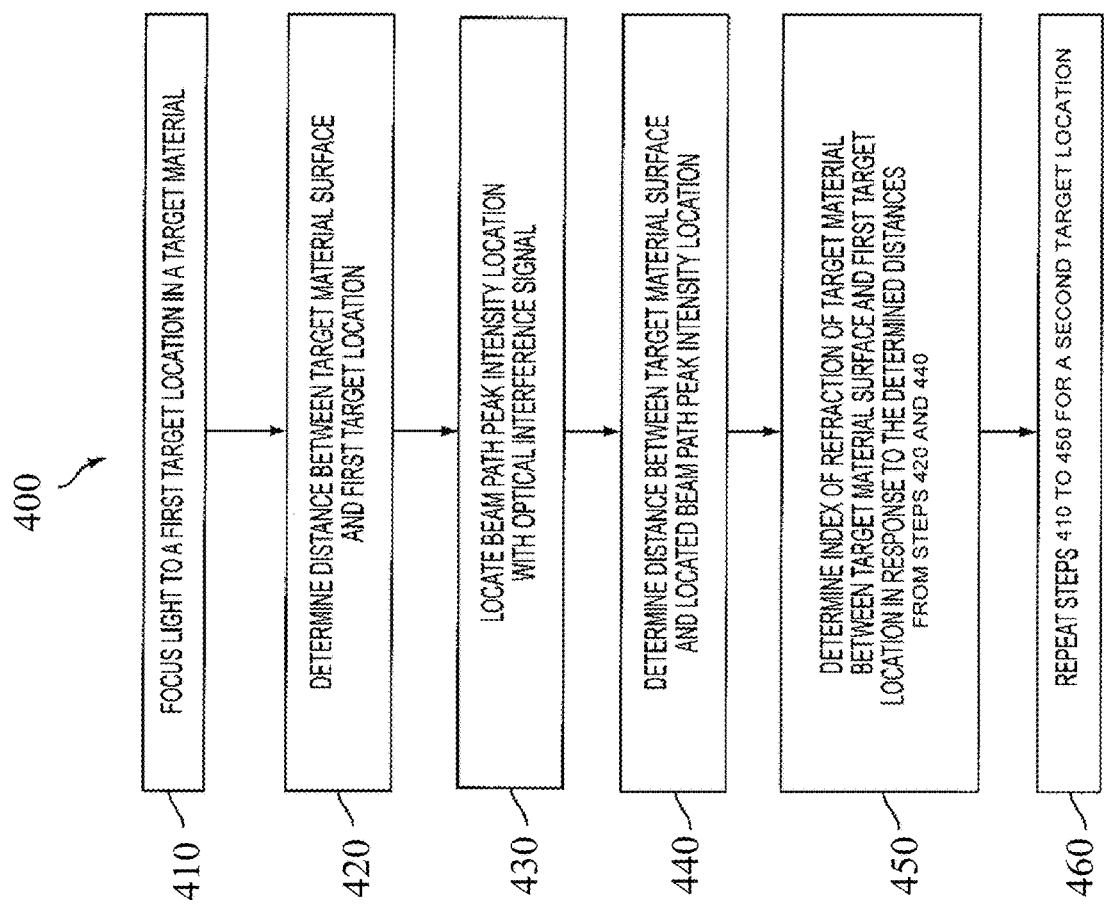
FIG. 11 shows a flow chart depicting a method for determining an index of refraction of a target material according to many embodiments.

FIG. 11 shows a flow chart depicting a method 300 for determining an index of refraction of a target material according to many embodiments.

In a step 410, light is focused to a first target location in a target material. As described herein, the focused light may comprise a beam 500, the first target location may comprise a target focal point 510, and the target material may comprise an anatomical structure of the eye 43 of a subject, such as the lens LE.

In a step 320, a distance between a surface of the target material and the first target location is determined. For example, the target material may comprise the lens LE and the surface of the target material may comprise the anterior surface of the lens LE. A user may direct the laser eye surgery system 2 to focus the beam 500 onto the target focal point 510. In response, the laser eye surgery system 2 may locate the target focal point 510 in response to predetermined refractive index data as described herein.

In many embodiments, the assumed index of refraction used by the laser eye surgery system 2 to calculate the position of the target focal point 510 may be referred to as $n_{assumed}$. The distance between the surface of the target material, e.g., the anterior surface of the lens LE, and the first target location, e.g., the target focal point 510, may be referred to as $D_{COMMAND}$. As described herein, the target focal point 510 may not be located in the same position as the actual focal point 520 due to refraction that the laser eye surgery system 2 and the ranging subsystem 46 may not account for. The distance between the surface of the target material, e.g., the anterior surface of the lens LE, and the actual focal point 520 may be referred to as $D_{ACTUAL}$. The actual index of refraction of the target material between the surface, e.g., the anterior surface of the lens LE, and the first target location, e.g., the target focal point 510, may be referred to as $n_{actual}$. In many embodiments, $D_{ACTUAL}$ is related to $D_{COMMAND}$ in accordance to the following equation: $D_{ACTUAL}=D_{COMMAND}*(n_{actual}/n_{assumed})$.

In a step 330, a peak intensity location of the beam path is located with an optical interference signal. For example, the ranging subsystem 46 may measure the intensity of the beam path along an axis, such as a vertical or Z-axis, through the target focal point 510 and may determine the location of peak intensity along this path. This peak intensity location may correspond to the location of the actual focal point 520.

In a step 340, a distance between the surface of the target material and the located beam path peak intensity location is determined. In many embodiments, an optical coherence tomography (OCT) system is used to determine intensity through the beam path. The distance between the surface of the target material, e.g., the anterior surface of the lens LE, and the located beam path peak intensity location may be referred to as $D_{OCT}$. As light may refract as it propagates through the target material to be read by the OCT system, the OCT system may account for this refraction using an assumed index of refraction which may be referred to as $n_{assumed}$. In many embodiments, $D_{OCT}$ is related to $D_{ACTUAL}$, in accordance with the following equation: $D_{OCT}=D_{ACTUAL}*(n_{actual}/n_{assumed})$.

In a step 350, the index of refraction of the target material between the target material surface and the first target location is determined in response to the determined distances from the steps 320 and 340. In many embodiments, this index of refraction comprises the average index of refraction of the material between the target material surface and the first target location. To determine this index of refraction, the above relationships or equations, $D_{ACTUAL}=D_{COMMAND}*(n_{actual}/n_{assumed})$ and $D_{OCT}=D_{ACTUAL}*(n_{actual}/n_{assumed})$, are applied. $D_{ACTUAL}$ is substituted for in the latter equation with the equivalent in the former equations to arrive at the equation: $D_{OCT}=D_{COMMAND}*(n_{actual}/n_{assumed})^2 \cdot n_{actual}$, or the index of refraction of the target material between the target material surface and the first target location, can then be calculated for using the rearranged equation: $n_{actual}=n_{assumed}*\sqrt{(D_{OCT}/D_{COMMAND})}$. The determined index of refraction can be mapped to the area of the lens of the eye.

In a step 360, the above steps 310 to 350 can be repeated for a second target location. The second target location may be in the same target material or a different target material. Also, instead of using the surface of the target material as the reference point for steps 320 and 340, the first target location may be used as the reference point for steps 320 and 340. As disclosed herein, the indices of refraction for a plurality of locations within a target material such as the lens LE can be measured to determine a refractive index profile of the target material, for example as shown in FIG. 5D.

One skilled in the art will appreciate that the above steps of the method 300 are by way of example. The ordering of the steps may be varied and one or more steps may be modified, added, or omitted without departing from the scope of the disclosure. A processor system of the laser eye surgery system 2 may comprise tangible medium embodying instructions for performing one or more steps of the method 300. Following the method 300, one or more of various surgical procedures may be performed on the eye. Such eye surgery procedures may include cataract surgery in response to the measured index or indices of refraction, retinal surgery in response to the measured index or indices of refraction, vitreo-retinal surgery in response to the measured index or indices of refraction, glaucoma surgery in response to the measured index or indices of refraction, refractive eye surgery in response to the measured index or indices of refraction, corneal surgery in response to the measured index or indices of refraction, and many other eye surgery procedures in response to the measured index or indices of refraction.

An example of refractive index measurement of an anatomical structure of the eye is now provided.

Figure 12:
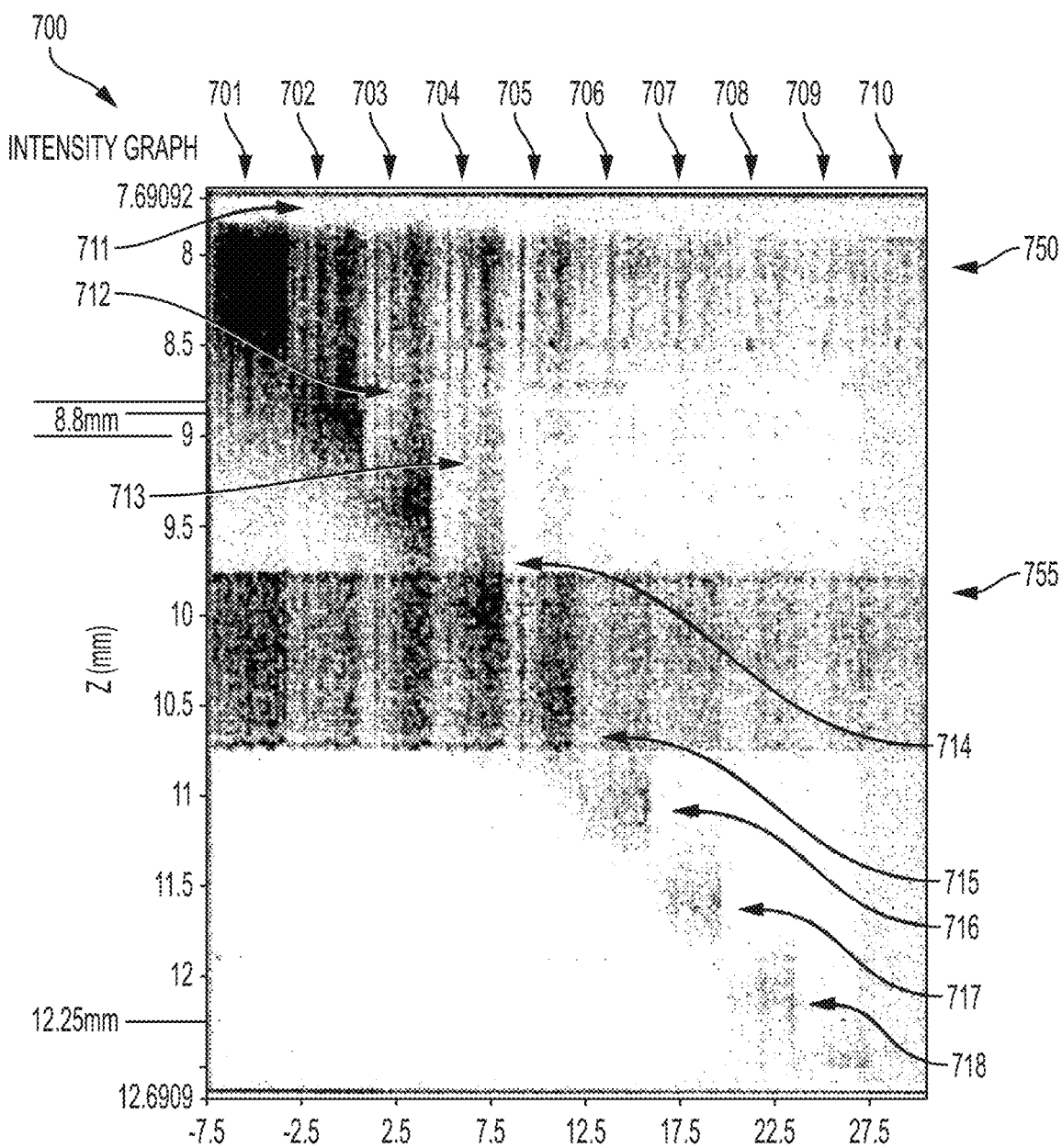
FIG. 12 shows an intensity graph of various beam paths through various anatomical structures of the eye for various desired focal points.

FIG. 12 shows an intensity graph 700 of various beam paths through various anatomical structures of the eye for various desired focal points. The beam path intensity profiles may be measured from the ranging subsystem 46 which may comprise an optical coherence tomography (OCT) system. The intensity graph 700 shows a first beam path intensity profile 701, a second beam path intensity profile 702, a third beam path intensity profile 703, a fourth beam path intensity profile 704, a fifth beam path intensity profile 705, a sixth beam path intensity profile 706, a seventh beam path intensity profile 707, an eight beam path intensity profile 708, a ninth beam path intensity profile 709, and a tenth beam path intensity profile 710. Each beam path intensity profile may correspond to a target focal point in the lens of an eye, with the higher numbered beam path profiles corresponding to deeper target focal points in the lens of the eye. For instance, the target focal point corresponding to the tenth beam profile 710 may be deeper than the target focal point corresponding to the ninth beam profile 709, which may be deeper than the target focal point corresponding to the eight beam profile 708, which may be deeper than the target focal point corresponding to the seventh beam profile 707, which may be deeper than the target focal point corresponding to the sixth beam profile 706, which may be deeper than the target focal point corresponding to the fifth beam profile 705, which may be deeper than the target focal point corresponding to the fourth beam profile 704, which may be deeper than the target focal point corresponding to the third beam profile 703, which may be deeper than the target focal point corresponding to the second beam profile 702, which may be deeper than the target focal point corresponding to the first beam profile 701. Each of these beam path intensity profiles may comprise a first high intensity band 750 and a second high intensity band 755. In many embodiments, the first and second high intensity bands 750, 755 comprise reflections from surfaces of one or more anatomical structures of the eye. For example, the first high intensity band 750 may comprise a reflection from the anterior surface of the cornea and the second high intensity band 755 may comprise a reflection from the posterior surface of the cornea.

The first beam path intensity profile 701 may comprise a peak intensity band 711 which may correspond to the focal point of the beam focused onto a first target focal point. The second beam path intensity profile 702 may comprise a peak intensity band 712 which may correspond to the focal point of the beam focused onto a second target focal point. The third beam path intensity profile 703 may comprise a peak intensity band 713 which may correspond to the focal point of the beam focused onto a third target focal point. The fourth beam path intensity profile 704 may comprise a peak intensity band 714 which may correspond to the focal point of the beam focused onto a fourth target focal point. The fifth beam path intensity profile 705 may comprise a peak intensity band 715 which may correspond to the focal point of the beam focused onto a fifth target focal point. The sixth beam path intensity profile 706 may comprise a peak intensity band 716 which may correspond to the focal point of the beam focused onto a sixth target focal point. The seventh beam path intensity profile 707 may comprise a peak intensity band 717 which may correspond to the focal point of the beam focused onto a seventh target focal point. The eight beam path intensity profile 708 may comprise a peak intensity band 718 which may correspond to the focal point of the beam focused onto an eighth target focal point. The ninth beam path intensity profile 709 may comprise a peak intensity band (not shown) which may correspond to the focal point of the beam focused onto a ninth target focal point. The tenth beam path intensity profile 710 may comprise a peak intensity band which may correspond to the focal point of the beam focused onto a tenth target focal point.

In the following example, the average index of refraction in the lens LE of the eye between two points can be calculated in response to the intensity graph 700. The peak intensity band 712 of the second beam path intensity profile 702 is located at a distance of 8.8 mm. The peak intensity band 718 of the eight beam profile 708 is located at a distance of 12.25 mm. The distance or difference between the two peak intensity bands 712 and 718 is therefore 3.45 mm. As described herein, this distance of 3.45 mm is regarded as $D_{OCT}$. The distance between the target focal point for the second beam path intensity profile 702 and the target focal point for the eight beam path intensity profile 708, or $D_{COMMAND}$, is 3 mm. That is, where the laser eye surgery system 2 is commanded to vary two focal points by 3 mm, the ranging subsystem 46 of the laser eye surgery system 2 detects the distance as 3.45 mm. As described herein, the index of refraction of the lens of the eye may be assumed. In this example, the assumed index of refraction, or $n_{assumed}$, is considered to be 1.3388. As described herein, the actual average index of refraction can be calculated in response to the aforementioned variables using the equation: $n_{actual} = n_{assumed} * \sqrt{D_{OCT}/D_{COMMAND}}$. In this example, $n_{actual}$, or the average index of refraction between the target focal points for the second beam path intensity profile 702 and the third beam path intensity profile 708, would therefore be $1.3388*\sqrt{3.45/3}$ or 1.4357. As described herein, the indices of refraction of the lens LE of the eye and other structures of the eye may vary, and by generating a refractive index profile of the lens LE of the eye and other structures of the eye, a laser eye surgery system 2 can more accurately place laser beam focal points within the eye such as to more accurately place incisions.

The laser eye surgery system 2 and the optical measurements obtained therewith may be used pre-operatively, i.e. before a cataract surgery or other surgical procedure, for, e.g., eye biometry and other measurements, diagnostics and surgical planning. Surgical planning may include one or more predictive models. In the one or more predictive models, one or more characteristics of the postoperative condition of the patient's eye or vision is modeled based on one or more selected from the group consisting of pre-operative measurements obtained from the laser eye surgery system 2, a contemplated surgical intervention, and on or more algorithms or models stored in the memory of the laser eye surgery system 2 and executed by the processor. The contemplated surgical intervention may include the selection of an IOL for placement, the selection of an IOL characteristic, the nature or type of incision to be used during surgery (e.g., relaxation incision), or one or more post-operative vision characteristics requested by the patient.

The laser eye surgery system 2 and the optical measurements obtained therewith may be used intra-operatively, i.e., during a cataract surgery or other surgical procedure, for, e.g., intraoperative eye diagnostics, determining IOL position and/or orientation, surgical planning, and control/or of a laser surgical system. For instance, in the case of laser cataract surgical procedure, any measurement data obtained preoperatively by the optical measurement instrument may be transferred to a memory associated with a cataract laser surgical system for use before, during or after either the placement of a capsulotomy, fragmentation or a patient's lens or IOL position and/or orientation during the cataract surgery. In this regard, conditions measured during the surgical procedure may be compared to a predicted condition of the patient's eye based on pre-operative measurements, and a difference between the predicted condition and the actual measured condition may be used to undertake additional or corrective actions during the cataract surgery or other surgical procedure. The corrective procedure may also be merely based on intraoperative measurements so that the actual measured condition dictates the action that is needed to provide the desired outcome.

The laser eye surgery system 2 and the optical measurements obtained therewith may be used postoperatively, i.e., after a cataract surgery or other surgical procedure, for, e.g., post-operative measurement, postoperative eye diagnostics, postoperative IOL position and/or orientation determinations, and corrective treatment planning if necessary. The postoperative testing may occur sufficiently after the surgery that the patient's eye has had sufficient time to heal and the patient's vision has achieved a stable, postsurgical state. A postoperative condition may be compared to one or more predicted condition performed pre-operatively, and a difference between the preoperatively predicted condition and the postoperatively measured condition may be used to plan additional or corrective actions during the cataract surgery or other surgical procedure. The corrective procedure may also be merely based on intraoperative measurements so that the actual measured condition dictates the action that is needed to provide the desired outcome.

The laser eye surgery system 2 preferably stores all the biometric data and postoperative information in an embedded database, so that the data contained in this database can be used to further optimize or generate new algorithms to improve future patient's outcomes. In certain embodiments, these algorithms are related to optimize actual lens position prediction, surgically induced astigmatism, IOL constants or personalized regressions to account for corneal spherical aberration in IOL power calculations for post-LASIK eyes.

The laser eye surgery system 2, including the corneal topography subsystem, the OCT subsystem and the ranging subsystem, utilizing a suitable operating sequence as disclosed herein, is operable to measure one, more than one or all of the following: ocular biometry information, anterior corneal surface information, posterior corneal surface information, anterior lens surface information, posterior lens surface information, lens thickness information, and lens position information. In some embodiments, the ocular biometry information may include a plurality of central corneal thicknesses (CCT), an anterior chamber depth (ACT), a lens thickness (LT), and an axial length (AL), any or all of which may be based on the measured index or refraction as described herein. This measurement data may be stored in memory 62 associated with controller 60. The plurality of characteristics may be measured intraoperatively, and where appropriate, preoperatively, and postoperatively.

In some embodiments, memory 62 associated with controller 60 may store intraocular lens (IOL) model data for a plurality of IOL models, each of the IOL models having associated with it a plurality of predetermined parameters selected from the group consisting of dioptic power, refractive index and dispersion, asphericity, toricity, echellete features, haptic angulation and lens filter. The IOL data may be used by one or more processors of laser eye surgery system 2, in conjunction with measurement data of a subject's eye obtained by laser eye surgery system 2, for cataract diagnostics or cataract treatment planning, which may include specifying and/or selecting a particular IOL for a subject's eye. For example, one or more processors of laser eye surgery system 2 may execute an algorithm which includes: accessing the plurality of IOL models stored in, and for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL for the subject's eye from the plurality of IOL models corresponding to the optimized IOL based on a predetermined criteria and the measured characteristics of the patient's obtained by the laser surgery system 2.

In some embodiments, one or more processors of laser eye surgery system 2 may execute an algorithm comprising: determining a desired postoperative condition of the subject's eye; empirically calculating a post-operative condition of the eye based at least partially on the measured eye characteristics; and predictively estimating, in accordance with an output of said empirically calculating and the eye characteristics, at least one parameter of an intraocular lens for implantation into the subject's eye to obtain the desired postoperative condition.

In many embodiments, the eye imaging and measurement system further comprises a memory operable to store Intraocular Lens ("IOL") Data, the IOL data including a plurality of dioptic power, anterior and posterior radius, IOL thickness, refractive index and dispersion, asphericity, toricity, echellete features, haptic angulation and lens filter.

In many embodiments, the eye imaging and measurement system further comprises a memory operable to store intraocular lens ("IOL") model data for a plurality of IOL models, IOL model having associated with a plurality of predetermined parameters selected from the group consisting of dioptic power, anterior and posterior radius, IOL thickness, refractive index and dispersion, asphericity, toricity, echellete features, haptic angulation and lens filter.

An improved system for selecting an intraocular lens (IOL) for implantation, comprises: a memory operable to store data acquired from each of the corneal topography subsystem, a ranging subsystem and the Optical Coherence Tomography subsystem, wherein the stored data includes a plurality of ocular biometry information, anterior corneal surface information, posterior corneal surface information, anterior lens surface information, and posterior lens surface information, lens thickness information, and lens position information; the memory further operable to store intraocular lens ("IOL") model data for a plurality of IOL models, IOL model having associated with it a plurality of predetermined parameters selected from the group consisting of dioptic power, anterior and posterior radius, IOL thickness, refractive index and dispersion, asphericity, toricity, echellete features, haptic angulation and lens filter; and a processor coupled to the memory, the processor deriving the treatment of the eye of the patient applying, for each of the plurality of identified IOL Model, to: (1) predict a position of one of the identified IOL Models when implanted in the subject eye, based on the plurality of characteristics; (2) simulate the subject eye based on the plurality of IOL predetermined parameters and the predicted IOL position; (3) perform one or more of ray tracing and an IOL spherical equivalent (SE) and cylinder (C) power calculation, as well as optionally, to determine the optimum IOL orientation based on said eye model; and (4) propose one IOL power for one or more IOL models from the plurality of IOLs corresponding to the optimized IOL(s) based on predetermined criteria; and (5) show the simulated optical quality and/or visual performance provided by each of the proposed IOL models for distance and/or for any other vergence and/or field angle.

A method of selecting an intraocular lens (IOL) to be implanted in a subject's eye, comprising: measuring a plurality of eye characteristics comprising ocular biometry information obtained via the laser surgery system 2, anterior corneal surface information, posterior corneal surface information, anterior lens surface information, and posterior lens surface information, lens thickness information and lens position information; and for each of Intraocular Lens ("IOL") model having associated with it a plurality of predetermined parameters selected from the group consisting of dioptic power, refractive index and dispersion, anterior and posterior radius, IOL thickness, asphericity, toricity, echellete design, haptic angulation and lens filter: (1) modeling the subject eye with the intraocular lens; (2) simulating the subject eye based on the plurality of IOL predetermined parameters and the predicted IOL position; (3) performing a ray tracing and an IOL spherical equivalent (SE) and cylinder (C) power calculation, as well as determine the optimum IOL orientation based on said eye model; and (4) proposing one IOL power for one or more IOL models from the plurality of IOLs corresponding to the optimized IOL(s) based on predetermined criteria; and optionally (5) show the simulated optical quality and/or visual performance provided by each of the proposed IOL models for distance and/or for any other vergence and/or field angle.

A tangible computer-readable storage device storing computer instructions which, when read by a computer, cause the computer to perform a method comprising: receiving a plurality of eye characteristics comprising ocular biometry information, anterior corneal surface information, posterior corneal surface information, anterior lens surface information, and posterior lens surface information, lens thickness information and lens position information; for each of Intraocular Lens ("IOL") model having associated with it a plurality of predetermined parameters selected from the group consisting of dioptic power, refractive index and dispersion, anterior and posterior radius, IOL thickness, asphericity, toricity, echelette design, haptic angulation and lens filter: (1) simulating a geometry of the subject eye with each of the plurality of intraocular lenses (IOL) implanted, in accordance with the plurality of eye characteristics; (2) performing a ray tracing and an IOL spherical equivalent (SE) and cylinder (C) power calculation, as well as optionally determining the optimum IOL orientation based on said eye model; (3) proposing one IOL power for one or more IOL models from the plurality of IOLs corresponding to the optimized IOL(s) based on predetermined criteria; and optionally (4) showing the simulated optical quality and/or visual performance provided by each of the proposed IOL models for distance and/or for any other vergence and/or field angle.

A method of predicting the intraocular lens position comprising: determining a plurality of eye characteristics before cataract surgery, comprising ocular biometry information, anterior corneal surface information, posterior corneal surface information, anterior lens surface information, and posterior lens surface information, lens thickness information and lens position information; determining a plurality of eye characteristics after cataract surgery, comprising ocular biometry information, anterior corneal surface information, posterior corneal surface information, anterior IOL surface information, and posterior IOL surface information, IOL tilt information, and IOL position information; calculating or measuring, based on a mathematical relationship, a distance from the apex or from the retina to a plane of the intraocular lens after an ocular surgical procedure; calculating an optical power of the intraocular lens suitable for providing a predetermined refractive outcome; wherein a mathematical relationship is found between the preoperative and postoperative eye characteristics that accurately predict the measured distance from the apex or from the retina to the plane where the intraocular lens is. In a certain embodiment, the method herein described to predict the IOL position may depend on the IOL model and/or patient's biometric configurations.

An improved system for planning a refractive treatment of an eye of a patient, the system comprising: a memory operable to store eye measurement data comprising ocular biometry information, anterior corneal surface information, posterior corneal surface information, anterior lens surface information, and posterior lens surface information, and lens position information; a processor coupled to the memory, the processor deriving the treatment of the eye of the patient applying an effective treatment transfer function, wherein the effective treatment transfer function is derived from, for each of a plurality of prior eye treatments, a correlation between a pre-treatment vector characterizing the eye measurement data before treatment, and a post-treatment vector characterizing post-treatment eye measurement data of the associated eye; an output coupled to the processor so as to transmit the treatment to facilitate improving refraction and/or higher order aberration and/or optical quality of the eye of the patient for one or more multiple vergences and/or field angles. The processor preferably comprises tangible media embodying machine readable instructions for implementing the derivation of the treatment.

An improved method for planning a refractive treatment of an eye of a patient, the system comprises: measuring a plurality of ocular biometry information, anterior corneal surface information, posterior corneal surface information, anterior lens surface information, and posterior lens surface information, lens thickness information and lens position information.

A method of customizing at least one parameter of an intraocular lens, comprising: measuring a plurality of eye characteristics comprising ocular biometry information, anterior corneal surface information, posterior corneal surface information, anterior lens surface information, and posterior lens surface information, and lens position information; determining a desired postoperative condition of the eye; empirically calculating a post-operative condition of the eye based at least partially on the measured eye characteristics; and predictively estimating, in accordance with an output of said empirically calculating and the eye characteristics, the at least one parameter of the intraocular lens to obtain the desired postoperative condition.

In some embodiments, the system further comprises a processor configured to execute an algorithm. The algorithm comprises, for each of the IOL models: (1) modeling the subject's eye with an intraocular lens corresponding to the IOL model and the measured characteristics of the subject's eye; (2) simulating the subject's eye based on the plurality of IOL predetermined parameters and the predicted IOL position; (3) performing one of a ray tracing and a power calculation based on said model of the subject's eye; and (4) selecting an IOL from the plurality of IOL models corresponding to the optimized IOL based on a predetermined criteria.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art that the embodiments are provided by way of example only numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

The foregoing description, for purpose of explanation, has been described with reference to specific examples. However, the illustrative discussions above are not intended to be exhaustive or to limit the invention to the precise forms disclosed. Many modifications and variations are possible in view of the above teachings. The examples were chosen and described in order to best explain the principles of the invention and its practical applications, to thereby enable others skilled in the art to best utilize the invention and various examples with various modifications as are suited to the particular use contemplated.

We claim:

1. An ophthalmic measurement and laser surgery system for measuring a patient's eye, comprising:
   a laser source configured to produce a pulsed laser beam;
   a corneal topography determining subsystem;
   an axis determining subsystem;
   a ranging subsystem comprising an Optical Coherence Tomographer (OCT);
   a refractive index determining subsystem;
   each of the laser source, the corneal topography determining subsystem, the axis determining subsystem, and the refractive index determining subsystem under the operative control of a controller, wherein the controller is configured to:
   operate the corneal topography determining subsystem to obtain corneal surface information of the patient's eye;
   operate the axis determining subsystem to identify one or more ophthalmic axes of the patient's eye;
   operate the OCT to sequentially scan the eye in a plurality of OCT scan patterns, the plurality of scan patterns configured to determine an axial length of the patient's eye;
   operate the refractive index determining subsystem so to determine an index of refraction of one or more ophthalmic tissues of the patient's eye; and
   modify a structural information of at least one of the corneal surface information, ophthalmic axis information, and axial length based on the determined index of refraction of the one or more ophthalmic tissues of the patient's eye.

2. The system of claim 1, wherein the corneal surface information comprises one or more selected from the group consisting of anterior corneal surface information and posterior corneal surface information.

3. The system of 1, wherein the one or more ophthalmic axes is selected from the group consisting of an optical axis, a treatment axis, a visual axis, and a fiducial marker axis.

4. The system of claim 1, wherein the controller is configured to sequentially scan the eye in a plurality of OCT scan patterns, each scan pattern being at a different axial depth of a patient's eye.

5. The system of claim 4, wherein the plurality of scan patterns comprise an anterior segment OCT scan pattern at or near a location of a cornea of the patient, a lenticular OCT scan pattern at or near a location of a lens, and a retinal OCT scan patter at or near a location of a retina.

6. The system of claim 1, wherein the controller is further configured to perform a plurality of imaging scan patterns comprising a lenticular OCT scan segment scan pattern suitable to measure a plurality of lens information selected from the group consisting of a lens thickness, an anterior lens surface, a posterior lens surface, and a lens equator; and wherein at least one of the lens information, the corneal surface information, ophthalmic axis information, and axial length is modified based on the determined index of refraction, thereby obtaining modified structural information.

7. The system of claim 6, wherein the plurality of imaging scan patterns comprise an anterior segment OCT scan pattern suitable to measure a plurality of corneal surface information selected from the group consisting of an anterior corneal surface, a posterior corneal surface, a corneal pachymetry, a central corneal thickness, and anterior chamber depth of a patient's eye, and wherein the corneal surface information is modified based on the determined index of refraction.

8. The system of claim 6, wherein the plurality of imaging scan patterns comprise a retinal OCT segment scan pattern suitable to measure at least one of an axial length and retinal layer thickness information, and wherein the at least one of the axial length and retinal layer thickness information is modified based on the determined refractive index.

9. The system of claim 6, wherein the controller is configured to perform a ray tracing of subject eye based at least in part on the lens information and the modified structural information.

10. The system of claim 1, wherein the ophthalmic tissue comprises an optically transmissive tissue structure of an eye of a subject.

11. The system of claim 10, wherein the optically transmissive tissue structure of the eye comprises one or more of a tear film, a cornea, an aqueous humor, a lens, an anterior lens capsule, a lens cortex, an anterior portion of the lens cortex, a posterior portion of the lens cortex, a lens nucleus, a posterior lens capsule, or a vitreous humor.

12. The system of claim 1, further comprising: a processor; and a memory operable to store data acquired from each of the corneal topography determining subsystem, the axis determining subsystem, and the OCT, wherein the stored data includes a plurality of corneal surface information, the axis information, and the axial length of the eye.

13. The system of claim 12, further comprising a memory operable to store Intraocular Lens ("IOL") Data, the IOL data including a plurality of dioptic power, anterior and posterior radius, IOL thickness, refractive index and dispersion, asphericity, toricity, echelette features, haptic angulation and lens filter.

14. The system of claim 12, wherein the memory is further operable to store a plurality of Intraocular Lens ("IOL") models, each IOL model having associated with it a plurality of predetermined parameters selected from the group consisting of dioptic power, refractive index and dispersion, anterior and posterior radius, IOL thickness, asphericity, toricity, echelette design, haptic angulation and lens filter, and wherein for each IOL model, the controller is programmed to execute a program to: (1) model the subject eye with an intraocular lens based in part on the stored data; (2) simulate the subject eye based on the plurality of IOL predetermined parameters and a predicted IOL position; (3) perform a ray tracing and determine the optimum IOL orientation based on said eye model; and (4) identify one IOL power for one or more IOL models from the plurality of IOLs corresponding to the optimized IOL(s) based on predetermined criteria.

15. The system of claim 12, wherein the memory is further operable to store a plurality of Intraocular Lens ("IOL") models, each IOL model having associated with it a plurality of predetermined parameters selected from the group consisting of dioptic power, refractive index and dispersion, anterior and posterior radius, IOL thickness, asphericity, toricity, echelette design, haptic angulation and lens filter, and wherein for each IOL model, the controller is programmed to execute a program to: (1) model the subject eye with the intraocular lens based on the stored data; (2) simulate the subject eye based on the plurality of IOL predetermined parameters and a predicted IOL position; (3) perform a ray tracing and determine the optimum IOL orientation based on said eye model; and (4) identify one IOL model from the plurality of IOLs corresponding to the optimized IOL based on predetermined criteria.

16. The system of claim 1, further comprising: a scanner, wherein the controller is configured to operate the scanner to deflect the laser beam to one or more treatment patterns, the treatment pattern configured so to incise in one or more ocular tissues in the eye of the patient.

17. The system of claim 16, wherein the one or more treatment patterns is a capsulotomy treatment pattern configured to incise a capsulotomy in the lens capsule.

18. The system of claim 16, wherein the one or more treatment patterns is a lens fragmentation treatment pattern configured to fragment the lens.

19. The system of claim 16, wherein the one or more treatment patterns is a relaxing incision treatment pattern.

20. The system of claim 16, wherein the one or more treatment patterns is a cataract incision treatment pattern.

21. The system of claim 16, wherein the one or more treatment patter is a sideport incision treatment pattern.

* * * * *